US00RE51086E

(19) United States
(12) Reissued Patent
Bowie et al.

(10) Patent Number: US RE51,086 E
(45) Date of Reissued Patent: *Oct. 20, 2026

(54) MOLECULAR RHEOSTAT FOR COFACTOR BALANCE

(71) Applicant: The Regents of the University of California, Oakland, CA (US)

(72) Inventors: James U. Bowie, Los Angeles, CA (US); Tyler P. Korman, Sierra Madre, CA (US); Paul H. Opgenorth, Los Angeles, CA (US)

(73) Assignee: The Regents of the University of California, Oakland, CA (US)

( * ) Notice: This patent is subject to a terminal disclaimer.

(21) Appl. No.: 18/189,147

(22) Filed: Mar. 23, 2023

Related U.S. Patent Documents

Reissue of:

(64) Patent No.: 10,760,103
Issued: Sep. 1, 2020
Appl. No.: 16/342,849
PCT Filed: Oct. 18, 2017
PCT No.: PCT/US2017/057156
§ 371 (c)(1),
(2) Date: Apr. 17, 2019
PCT Pub. No.: WO2018/075624
PCT Pub. Date: Apr. 26, 2018

U.S. Applications:

(63) Continuation of application No. 17/822,623, filed on Aug. 26, 2022, which is an application for the reissue of Pat. No. 10,760,103.

(60) Provisional application No. 62/409,731, filed on Oct. 18, 2016.

(51) Int. Cl.

| | |
|---|---|
| ***C12P 7/16*** | (2006.01) |
| ***C12N 9/02*** | (2006.01) |
| ***C12N 9/12*** | (2006.01) |
| ***C12P 9/00*** | (2006.01) |
| ***C12P 13/06*** | (2006.01) |
| ***C12P 13/08*** | (2006.01) |

(52) U.S. Cl.
CPC ..... *C12P 7/16* (2013.01); *C12N 9/0008* (2013.01); *C12N 9/1217* (2013.01); *C12P 9/00* (2013.01); *C12P 13/06* (2013.01); *C12P 13/08* (2013.01); *C12Y 102/01012* (2013.01); *C12Y 207/02003* (2013.01)

(58) Field of Classification Search
CPC .. C12P 7/16; C12P 13/06; C12P 13/08; C12N 9/0008; C12N 9/1217; C12Y 102/01012; C12Y 207/02003
See application file for complete search history.

(56) References Cited

U.S. PATENT DOCUMENTS

2006/0075522 A1 4/2006 Cleveland et al.

FOREIGN PATENT DOCUMENTS

WO 2015/153929 A2 10/2015 ..... C12N 9/0008
WO 2017/015429 A2 1/2017

OTHER PUBLICATIONS

Anonymous, "Phosphoglycerate kinase. *Geobacillus stearothermophilus* (*Bacillus stearothermophilus*)", UniProtKB, (Aug. 1, 1992), Database Accession No. P18912, Aug. 1, 1992, 4 pages.
Bor, Henrietta, Office Action, Canadian Intellectual Property Office, Application No. 3,043,588, Feb. 20, 2024.
Centeno-Leija, Sara et al.: "Improving poly-3-hydroxybutyrate production in *Escherichia coli* by combining the increase in the NADPH pool and acetyl-CoA availability", Antonie Van Leeuwenhoek, Feb. 6, 2014, vol. 105, No. 4, pp. 687-696.
Choi, Sung-ho, Office Action, Korean Intellectual Property Office, Application No. 10-2019-7013988, Mar. 21, 2024.
Conlan, Brendon, Office Action, Australia Intellectual Property Office, Application No. 2017345324, Feb. 15, 2022.
Fillinger et al., "Two Glyceraldehyde-3-phosphate Dehydrogenases with Opposite Physiological Roles in a Nonphotosynthetic Bacterium", J. Biol Chem, May 12, 2000, vol. 275, No. 19, pp. 14031-14037.
Fortes, Maria Hercilia Paim, Office Action, Brazil Patent Office, Application No. BR112019007868-1, Sep. 23, 2022.
Iancu, Liviu, Jr., "Cell-Free Biofuel Production using an In Vitro Synthetic Biochemistry Platform and Quantification of Isobutanol Tolerance of Synthesis Enzymes", Thesis, Los Angeles, 2016, 68 pages.
Jiang et al., "Metabolic engineering of Corynebacterium glutamicum for increasing the production of L-ornithine by increasing NADPH availability", Journal of Industrial Microbiology and Biotechnology, Jul. 9, 2013, vol. 40, No. 10, pp. 1143-1151.
Maceachran, Daniel P. et al., "The Rhodococcus opacus TadD protein mediates triacylglycerol metabolism by regulating intracellular NAD(P)H pools", Microbial Cell Factories, Nov. 9, 2013, vol. 12, No. 1, pp. 1-12.
Mohri, Mineko, International Preliminary Report on Patentability and Written Opinion, The International Bureau of WIPO, May 2, 2019.
Opgenorth, P. et al., "A synthetic biochemistry molecular purge valve module that maintains redox balance", Nat Commun, Jun. 17, 2014, vol. 5, 8 pages.
Orenshtein, Liya, Dr., Office Action, Israel Patent Office, Application No. 266019, Sep. 20, 2022.
Schroder, Gunnar, Extended European Search Report, European Patent Office, Application No. 17862069.6, Jun. 12, 2020.
Shirai, Mikaho, Office Action, Japan Patent Office, Application No. 2019-542353, Sep. 7, 2021.
Somkuwar, Manoj G., Office Action, Intellectual Property Office of India, Application No. 201917019483, Apr. 18, 2023.

(Continued)

*Primary Examiner* — Lora E Barnhart Driscoll
(74) *Attorney, Agent, or Firm* — Gavrilovich, Dodd & Lindsey LLP

(57) ABSTRACT

The disclosure provides a metabolic pathway for producing a metabolite, the metabolic pathway having a co-factor regulatory system for cofactor utilization in the metabolic pathway.

19 Claims, 8 Drawing Sheets

Specification includes a Sequence Listing.

(56) References Cited

OTHER PUBLICATIONS

Song, Meng, Office Action, China National Intellectual Property Administration, Application No. 2017800774822, Feb. 9, 2023.

Takeno et al., "L-Lysine production independent of the oxidative pentose phosphate pathway by corynebacterium glutamicum with the *Streptococcus mutans* gapN gene", Metabolic Engineering, Sep. 1, 2016, vol. 37, pp. 1-10.

Tan, John, Office Action, Singapore Intellectual Property Office, Application No. 11201903429Q, Sep. 21, 2020.

Valladares, Maria Gabriela Cabrera, Office Action, Mexican Intellectual Property Office, Application No. MX/a/2019/004427, Sep. 19, 2023.

Young, Lee W., International Search Report and Written Opinion, United States Patent and Trademark Office, PCT/US17/57156, Mar. 8, 2018.

Mohri, Mineko, International Preliminary Report on Patentability and Written Opinion, The International Bureau of WIPO, dated May 2, 2019.

Fillinger et al., "Two Glyceraldeyhyde-3-phosphate Dehydrogenases with Opposite Physiological Roles in a Nonphotosynthetic Bacterium", J. Biol. Chem., May 12, 2000, vol. 275, No. 19, pp. 14031-14037.

Iancu, "Cell-Free Biofuel Production using an In Vitro Synthetic Biochemistry Platform and Quantification of Isobutanol Tolerance of Synthesis Enzymes", University of California, Los Angeles Thesis published Jan. 1, 2016, 70 pages, Available on the internet: < https://cloudfront.escholarship.org/dist/prd/content/qt3nt366qc/qt3nt366qc.pdf>.

UniProtKB P18912.PGC_Geose. Aug. 1, 1992 [retrieved Feb. 20, 2018]. Available on the internet: <https://www.uniprot/P18912>.

Young, Lee W., International Search Report and Written Opinion, United States Patent and Trademark Office, PCT/US17/57156, dated Mar. 8, 2018.

Centeno-Leija, Sara et al., "Improving poly-3-hydroxybutyrate production in *Escherichia coli* by combining the ncrease in the NADPH pool and acetyl-CoA availability", Antonie Van Leeuwenhoek, vol. 105, No. 4, Feb. 6, 2014, pp. 687-696.

Jiang et al, "Metabolic engineering of Corynebacterium glutamicumfor increasing the production ofl-omithine by increasing NADPH availability", Journal of Industrial Microbiology and Biotechnology, Basingstoke, GB, vol. 40, No. 10, Jul. 9, 2013, pp. 1143-1151.

Maceachran, Daniel P. et al., "The Rhodococcus opacus TadD protein mediates triacylglycerol metabolism by regulating intracellular NAD (P)H pools," Microbial Cell Factories, vol. 12, No. 1, 104, Nov. 9, 2013, pp. 1-12.

Schroder, Gunnar, Search Report, European Patent Office, Application No. 17862069.6, dated Jun. 12, 2020.

Takeno et al., "L-Lysine production independent of the oxidative pentose phosphate pathway by Corynebacterium glutamicum with the Streptococcus mutans gapN gene", Metabolic Engineering, vol. 37, Sep. 2016, pp. 1-10.

MOLECULAR RHEOSTAT FOR COFACTOR BALANCE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This *application is a continuation reissue of application Ser. No. 17/822,623, meaning it is a continuation of reissue application Ser. No. 17/822,623, and is also a reissue application of US. Pat. No. 10,760,103 issued Sep. 1, 2020, which* is a U.S. National Phase Application filed under 35 U.S.C. § 371 and claims priority to International Application No. PCT/US2017/057156, filed Oct. 18, 2017, which application claims priority to U.S. Provisional Application Ser. No. 62/409,731, filed Oct. 18, 2016, the disclosures of which are incorporated herein by reference.

STATEMENT REGARDING FEDERALLY SPONSORED RESEARCH

This invention was made with Government support under [Grant No.] DE-AR0000556, awarded by the Department of Energy. The Government has certain rights in the invention.

*More than one reissue application has been filed for the reissue of U.S. Pat. No. 10,760,103. This is an application for reissue of U.S. Pat. No. 10,760,103, and is a continuation of application Ser. No. 17/822,623, filed on Aug. 26, 2022, which is also an application for reissue of U.S. Pat. No. 10,760,103.*

INCORPORATION BY REFERENCE OF SEQUENCE LISTING

Accompanying this filing is a Sequence Listing entitled [“Sequence_ST25.txt”] *“00011-087US1”*, created on [Oct. 18, 2017] *Aug. 26, 2022* and having [56,906] *20,575* bytes of data, machine formatted on IBM-PC, MS-Windows operating system. The sequence listing is hereby incorporated by reference in its entirety for all purposes.

TECHNICAL FIELD

The disclosure provides engineered pathways for chemical production using a molecular rheostate for ATP balance.

BACKGROUND

Over the past decades there has been a keen interest in engineering cellular metabolism for the production of “green” chemicals that could ween us off of our reliance on petrochemicals. One method is to perform a desired biochemical conversions with purified enzymes or cell extracts. Cell free metabolic systems have many advantages over in vivo efforts such as continuous product production, ease of product removal, near 100% yields, and no cell toxicity issues.

Building cell free pathways that can economically sustain high flux for long periods of time without the metabolic regulatory systems that exist in cells requires new design principles, a field referred to as “synthetic biochemistry”. A key consideration in synthetic biochemistry system design is the generation, regulation and recycling of high energy cofactors such as ATP, NADH and NADPH. Generally high energy cofactors are generated in a catabolic or breakdown phase (e.g. glycolysis), then utilized and regenerated in an anabolic or build phase where the desired chemicals are constructed. The simplest way to design synthetic biochemistry systems is to demand perfect stoichiometry, so that if two ATP are generated in the breakdown phase, then two ATP are utilized in the build phase. Stoichiometric systems can allow flux through the pathway for a period of time, but the second law of thermodynamics dictates that they will eventually wind down as ATP is hydrolyzed or NADH is oxidized by undesired side reactions.

SUMMARY

The disclosure provides a recombinant, artificial or engineered metabolic pathway comprising a plurality of enzymatic steps that converts a substrate to a product, wherein the pathway comprises a non-naturally occurring molecular rheostat system the alternates between or simultaneously uses a first cofactor pathway for the production of a metabolite and a second cofactor pathway for the production of the metabolite depending upon cofactor availability. In one embodiment, the pathway comprises: (a) a first enzymatic step that converts a first metabolite to a second metabolite using a first co-factor; (b) a second enzymatic step that converts the first metabolite to the second metabolite using a first co-factor and second co-factor or second co-factor; wherein the first enzymatic step is active when the second co-factor level is low and wherein the second enzymatic step is active when the second co-factor level is high. In another or further embodiment, the first cofactor is an oxidizing/reducing co-factors and the second cofactor is $P_i$. In still another embodiment of any of the foregoing embodiments, the oxidizing/reducing co-factors are $NAD^+$/NADH, $NADP^+$/NADPH or $FAD^+$/FADH. In still another embodiment of any of the foregoing embodiments, the first cofactor comprises $NADP^+$/NADPH. In still another embodiment of any of the foregoing embodiments, the metabolic pathway comprises the conversion of glyceraldehyde-3-phosphate to 3-phosphoglycerate. In still another embodiment of any of the foregoing embodiments, the metabolic pathway produces a metabolite selected from the group consisting of isobutanol, 3-methyl-1-butanol, leucine, and valine. In still another embodiment of any of the foregoing embodiments, the pathway comprises the conversion of glyceraldehyde-3-phosphate to 1,3-bisphosphoglycerate and 1,3-bisphosphoglycerate to 3-phosphoglycerate. In still another embodiment of any of the foregoing embodiments, the pathway comprises (i) an enzyme that converts glyceraldehyde-3-phosphate (G3P) and $NADP^+$ to 3-phosphoglycerate (3PG) and NADPH; and (ii) an enzyme that converts glyceraldehyde-3-phosphate (G3P), $NADP^+$ and free phosphate (Pi) to 1,3-bisphosphoglycerate (1,3BPG) and (iii) an enzyme that converts 1,3 bisphosphoglycerate (1,3BPG) and ADP to 3-phophoglycerate and ATP. In still another embodiment of any of the foregoing embodiments, the enzyme of (i) comprises a NADP-dependent glyceraldehyde-3-phosphate dehydrogenase (GapN). In still another embodiment of any of the foregoing embodiments, the GapN is obtained from S. mutans. In still another embodiment of any of the foregoing embodiments, the enzyme of (ii) comprises a mutant glyceraldehyde-3-phosphate dehydrogenase (mGap) that comprises D34A/L35R/T36K mutations relative to SEQ ID NO:6. In still another embodiment of any of the foregoing embodiments, the enzyme of (ii) comprises a mutant glyceraldehyde-3-phosphate dehydrogenase (mGap) that has a sequence that is at least 95% identical to SEQ ID NO:6 and comprises D34A/L35R/T36K mutations. In still another embodiment of any of the foregoing embodiments, the enzyme of (iii) comprises enzyme commission number (EC number) EC 2.7.2.3. In still another embodiment of any of the foregoing embodiments, the enzyme of (iii) is a phosphoglycerate kinase. In still another embodiment of any of the foregoing embodiments, the phosphoglycerate kinase is a Pgk from G. stearothermophilus. In still another embodiment of any of the foregoing embodiments, the enzyme of (iii) has a sequence that is at least 95% identical to SEQ ID NO:7 and has phosphoglycerate kinase activity. In still another embodiment of any of the foregoing embodiments, the molecular rheostat comprise the enzymes of (i) a NADP-dependent glyceraldehyde-3-phosphate dehydrogenase (GapN), (ii) a mutant glyceraldenhyde-3-phosphate dehydrogenase that utilizes $NADP^+$ and (iii) a phosphoglycerate kinase. In still another embodiment of any of the foregoing embodiments, the pathway comprises (i) a polypeptide that catalyzes the production of glucose-6-phosphate (G6P) from glucose; (ii) a polypeptide that catalyzes the production of Fructose-6-phosphate (F6P) from glucose-6-phosphate (G6P); (iii) a polypeptide the catalyzes the conversion/phosphorylation of fructose-6-phosphate (F6P) to fructose-1,6-phosphate; (iv) a polypeptide that converts fructose-1,6-phosphate to two glyceraldehyde-3-phosphates (G3P); (v) a molecular rheostat comprising (a) an enzyme that converts glyceraldehyde-3-phosphate (G3P) and $NADP^+$ to 3-phosphoglycerate (3PG) and NADPH and (b) an enzyme that converts glyceraldehyde-3-phosphate (G3P), $NADP^+$ and free phosphate (Pi) to 1,3-bisphosphoglycerate (1,3BPG) and (c) an enzyme that converts 1,3 bisphosphglycerate (1,3BPG) and ADP to 3-phophoglycerate (3pG) and ATP; (vi) a polypeptide that converts 3-phosphoglycerate (3PG) to 2-phosphoglycerate (2PG); (vii) a polypeptide that converts 2-phosphoglycerate (2PG) to phosphoenolpyruvate (PEP); (viii) a polypeptide that converts phosphoenolpyruvate (PEP) to pyruvate; (ix) a polypeptide that converts pyruvate to acetolactate; (x) a polypeptide that converts acetolactate and NADPH to 2,3 dihydroxy-3-methyl butanoate and $NADP^+$; (xi) a polypeptide that converts 2,3 dihydroxy-3-methyl butanoate to 3-methyl-2-oxobutanoate; (xii) a polypeptide that converts 3-methyl-2-oxobutanoate to isobutanal and (xiii) a polypeptide that coverts isobutanal and NADPH to isobutanol and $NADP^+$. In still another embodiment of any of the foregoing embodiments, wherein the pathway is in a cell-free system. In still another embodiment of any of the foregoing embodiments, wherein the polypeptides are present in a cell-free system.

The disclosure also provides a recombinant polypeptide comprising a sequence that is at least 95% identical to SEQ ID NO:6 and comprises D34A/L35R/T36K mutations and has glyceraldehyde-3-phosphate dehydrogenase activity.

The disclosure provide a molecular rheostat switch that allows a metabolic system to preferentially proceed down one of two pathways depending upon cofactor balance. For example, in one embodiment, the pathway proceed down an enzyme path that doesn't produce ATP or one that does produce ATP depending upon the amount of free phosphate (Pi) in the system. The choice is regulated by free phosphate which is needed by the mGAP enzyme. Free phosphate is a proxy for the amount of ATP hydrolyzed to ADP in the system. Effectively the flow down the ATP generating pathway is turned up or down depending on the Pi concentration. The biochemical pathway can be used to produced various chemical and biofuels from a carbon source (e.g., glucose).

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

DETAILED DESCRIPTION

Figure 1:
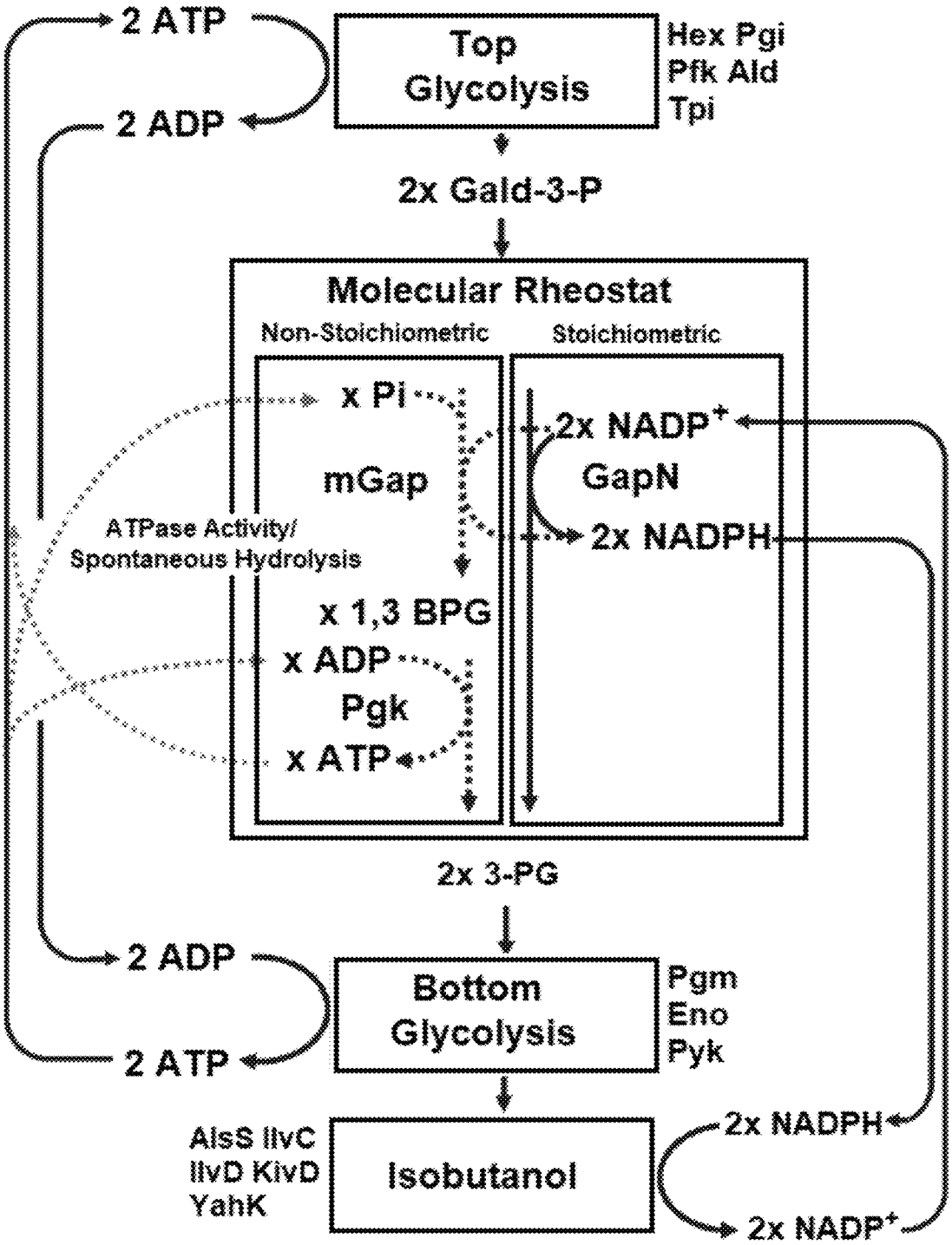
FIG. 1 provides a diagram of an in vitro pathway from glucose to isobutanol. The gapDH M6 and PGK scavenge inorganic phosphate and remake ATP that has been hydrolyzed in the system.

As used herein and in the appended claims, the singular forms "a," "and," and "the" include plural referents unless the context clearly dictates otherwise. Thus, for example, reference to "a polynucleotide" includes a plurality of such polynucleotides and reference to "the enzyme" includes reference to one or more enzymes, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

As used herein, an "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product. The disclosure provides in vitro biosynthetic pathways comprising a molecular rheostat which can optionally include a metabolic purge valve for the production of a desired product or intermediate. The disclosure also provides recombinant microorganism having a metabolically engineered pathway comprising a molecular rheostat and may further comprise a metabolic purge valve for the production of a desired product or intermediate.

As used herein a "cofactor" generally refers to a chemical compound or metabolite that is required for a protein's biological activity. The proteins are commonly enzymes, and cofactors assist in biochemical transformations. Cofactors include, but are not limited to, one or more inorganic ions, or a complex organic or metalloorganic molecule sometimes referred to as a coenzyme; most of which are derived from vitamins and from required organic nutrients in small amounts. Some enzymes or enzyme complexes require several cofactors. For example, the multienzyme complex pyruvate dehydrogenase at the junction of glycolysis and the citric acid cycle requires five organic cofactors and one metal ion: loosely bound thiamine pyrophosphate (TPP), covalently bound lipoamide and flavin adenine dinucleotide (FAD), and the cosubstrates nicotinamide adenine dinucleotide ($NAD^+$) and coenzyme A (CoA), and a metal ion ($Mg^{2+}$). Organic cofactors are often vitamins or are made from vitamins. Many contain the nucleotide adenosine monophosphate (AMP) as part of their structures, such as ATP, coenzyme A, FAD, and $NAD^+$.

An "enzyme" means any substance, typically composed wholly or largely of amino acids making up a protein or polypeptide that catalyzes or promotes, more or less specifically, one or more chemical or biochemical reactions.

The term "expression" with respect to a gene or polynucleotide refers to transcription of the gene or polynucleotide and, as appropriate, translation of the resulting mRNA transcript to a protein or polypeptide. Thus, as will be clear from the context, expression of a protein or polypeptide results from transcription and translation of the open reading frame.

A "metabolite" refers to any substance produced by metabolism or a substance necessary for or taking part in a particular metabolic process that gives rise to a desired metabolite, chemical, alcohol or ketone. A metabolite can be an organic compound that is a starting material (e.g., a carbohydrate, a sugar phosphate, pyruvate etc.), an intermediate in (e.g., acetyl-coA), or an end product (e.g., isobutanol, isoprene or PHB) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

As used herein, the term "metabolically engineered" or "metabolic engineering" involves rational pathway design and assembly of biosynthetic genes, genes associated with operons, and control elements of such polynucleotides, for the production of a desired metabolite, such as acetyl-CoA, higher alcohols or other chemical, in a microorganism, or in a cell-free system the rational pathway design and assembly of a biosynthetic pathway and co-factors for the production of a desired metabolite. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway. For example, in a cell free system a host cell expressing one or more enzymes used in the cell-free sytem can be further engineered to eliminate or remove competing pathway enzymes thereby removing contaminants or enzymes that may be present in a disrupted or cell-free preparation.

A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogenetic to the host organism, the polynucleotide can be codon optimized.

A "metabolic purge valve" refers to an engineered metabolic pathway that 'purges' excess metabolites and/or cofactors resulting in a recycling of the metabolite or co-factor for use in a primary metabolic pathway, e.g., by oxidizing a reduced cofactor thus "purging an abundance of reduced cofactors" etc.

A "molecular rheostat" refers to an enzymatic step that is only activated when a co-factor is at a level sufficient to turn-over the enzyme. In the absence of sufficient levels, the pathway proceeds by a secondary enzymatic step. For example, as shown in FIG. 1, a molecular rheostat can be made up of two competing pathway branches that eventually transform glyceraldehyde-3 phosphate (G3P) into 3-phosphoglycerate (3PG). One branch reduces a cofactor in the conversion of G3P which is regulated by oxidation/reduction levels, while the other branch generates ATP, while flow through the ATP generating branch is regulated by Pi levels.

Figure 3A:
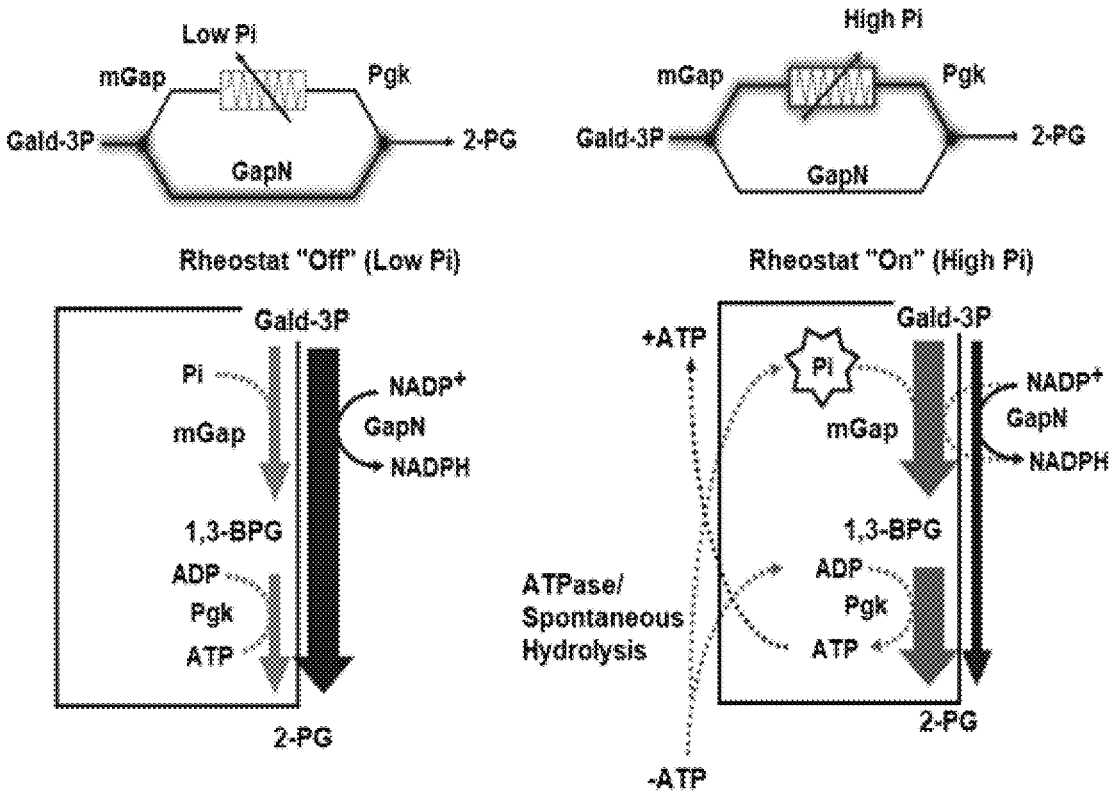
FIG. 3A-B shows a design of the "molecular rheostat" at glyceraldehyde-3-phosphate dehydrogenase. (A) Schematic of the molecular rheostat in glycolysis. (B) Model of the gapDH M6 crystal structure.
Figure 3B:
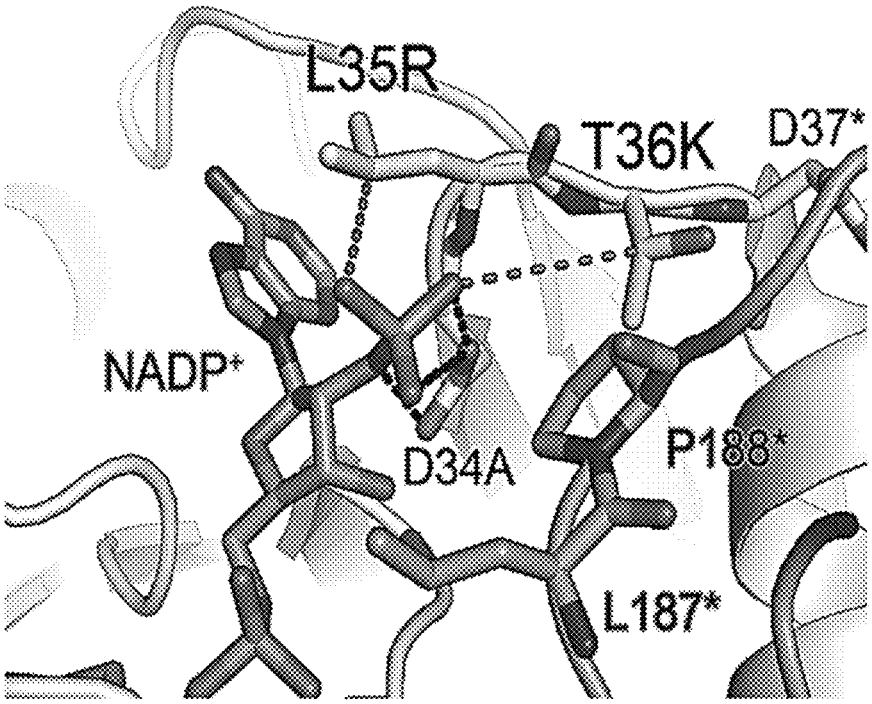
Figure 4A:
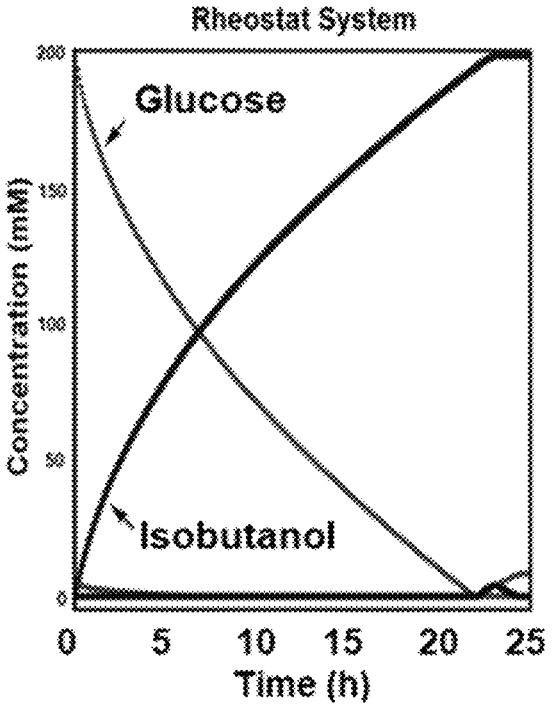
FIG. 4A-D shows a Copasi model of the rheostat pathway with ATPase activity modeled (A-B) and a Copasi model of the stoichiometric pathway with ATPase activity modeled (C-D). The initial conditions are set with 4 mM inorganic phosphate, gapDH M6/PGK activity held constant, and ATP hydrolysis was increased until the reaction died out. The reaction dies at an ATP hydrolysis to gapDH M6 ratio anything higher than 5:1.
Figure 4B:
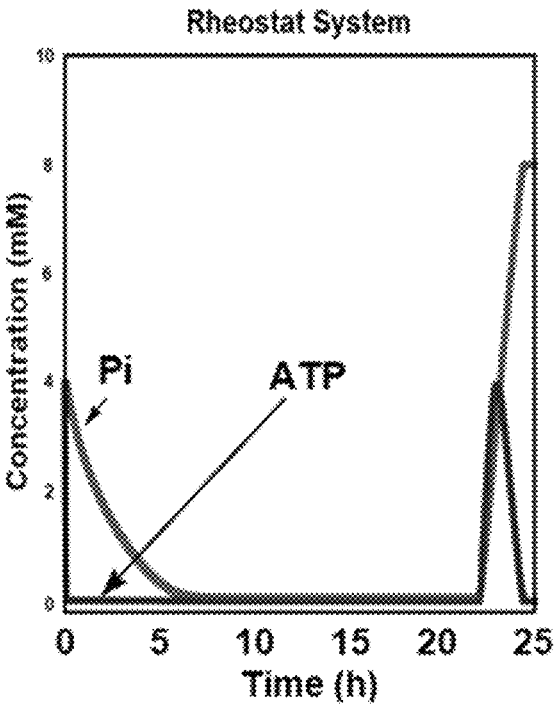
Figure 4C:
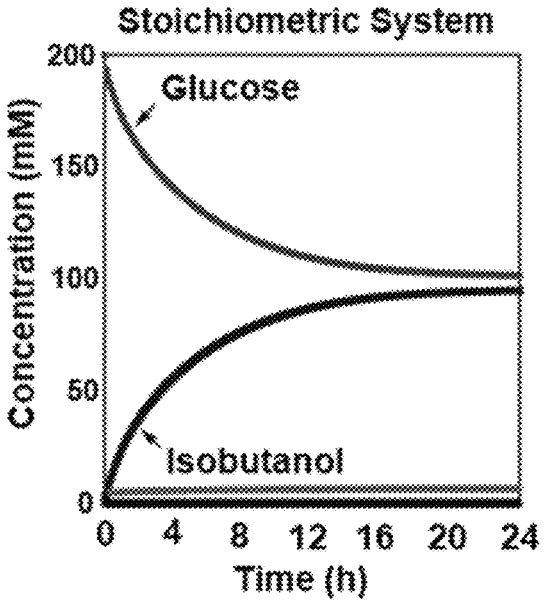
Figure 4D:
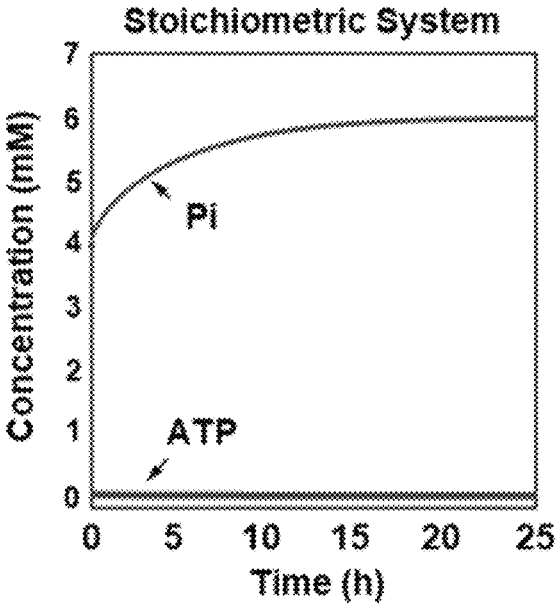

The first branch is made up of one enzyme, the non-phosphorylating GapN used in the stoichiometric pathway, which reduces $NADP^+$ to NADPH and converts G3P directly into 3PG without generating ATP. The second pathway is composed of two enzymes, an NADPH specific, phosphorylating glyceraldehyde-3-phosphate dehydrogenase (GapDH) and phosphoglycerate kinase (PGK), that also produces NADPH but first converts G3P into 1,3-bisphosphoglycerate (1,3BPG) followed by 3PG and ATP by the action of PGK. Therefore, the GapDH/PGK branch produces an additional ATP compared to the GapN only branch. The relative flow through the ATP generating branch of the rheostat is controlled by free Pi, which acts as a proxy for the amount of ATP hydrolyzed to ADP and Pi. The function of the rheostat is depicted in the simplest case, where no exogenous Pi is added to the reaction (FIG. 3A, left panel). In this case there is initially no free Pi and there can be no flux through the phosphorylating GAPDH. Thus, in the absence of Pi, all the flux passes through GapN branch. However, when ATP is hydrolyzed to ADP and Pi, the phosphorylating branch is then utilized. Thus, the rheostat senses the depletion of ATP and acts to restore ATP by utilizing the phosphorylating GAPDH branch (FIG. 3A, right panel).

The term "polynucleotide," "nucleic acid" or "recombinant nucleic acid" refers to polynucleotides such as deoxyribonucleic acid (DNA), and, where appropriate, ribonucleic acid (RNA).

A "protein" or "polypeptide", which terms are used interchangeably herein, comprises one or more chains of chemical building blocks called amino acids that are linked together by chemical bonds called peptide bonds. A protein or polypeptide can function as an enzyme.

The term "recombinant microorganism" and "recombinant host cell" are used interchangeably herein and refer to microorganisms that have been genetically modified to express non-expressed or over-express endogenous polynucleotides, or to express non-endogenous sequences, such as those included in a vector. The polynucleotide generally encodes a target enzyme involved in a metabolic pathway for producing a desired metabolite as described herein, but may also include protein factors necessary for regulation or activity or transcription. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism. It should also be understood that the recombinant microorganism can be used as a source of the polypeptide and that the recombinant microorganism need not have the full pathway for the generation of a desired metabolite. Rather, a plurality of recombinant microorganisms each having one or more, but not all, of the polypeptide for a metabolic pathway can be cocultured to produce the desired metabolite or can be disrupted and the cell-free milieu used or the expressed polypeptide isolated from each of the recombinant microorganisms.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, but also intermediate and end product metabolites used in a pathway as described herein. In addition, a substrate can be an oxidized or reduced co-factor or a factor that is phosphorylated or de-phosphorylated.

Metabolic engineering and synthetic biology have been employed for the production of high value chemicals but have not been as successful as hoped in meeting the stringent economics of large scale commodity chemical manufacturing. Microbial systems are often hampered by a variety of technical challenges that make it hard to achieve cost competitiveness, including poor yields due to competing pathways; low productivity caused by slow growth rates or difficulties in pathway optimization; contaminating microbial growth; product toxicity; and expensive product isolation.

As demonstrated herein, one approach to overcome these difficulties is to perform complex biochemical transformations using mixtures of enzymes in a reaction vessel or flow system rather than within a cell. Building single, dedicated pathways in vitro can eliminate side reactions that occur in the cell, so that nearly 100% yields and fast reaction times are possible. In vitro biochemical systems also allow for more precise control over optimization and product toxicity problems can be more easily diagnosed and mitigated. Moreover, product extraction can be more facile.

Traditionally, in vitro pathway construction has been relegated to use as a research tool or in applications that require only 1-3 enzymes for the production of chiral compounds and other high value chemicals. Improvements in protein expression and access to stable enzymes have made more complex systems possible. In vitro biotransformation systems have been reported in recent years involving systems of over thirty enzymes. One of the first modern studies in this area was an artificial pathway that produced hydrogen from starch. The concept was recently advanced with a creative system that generated hydrogen from cellobiose at nearly 100% yields. In another effort, hyper-thermophilic glycolysis enzymes were heterologously expressed, heat purified, and assembled to convert glucose to n-butanol in 82% yield. In another study, an elegantly simplified non-phosphorylative Entner-Doudoroff pathway from hyper-thermophilic archaea was constructed to produce ethanol and isobutanol in ~55% yields. These pioneering studies illustrate the flexibility of synthetic biochemistry and the potential for high yields.

Maintaining proper cofactor balance is an essential part of generating flux and providing a driving force through an enzymatic pathway. In vivo, the enzymatic specificity for the cofactors NADH/NADPH and/or ADP/ATP are typically used to control the carbon flux through catabolic and anabolic pathways respectively. Organisms typically sense the reduction state of these cofactors and use this information to up-regulate or down-regulate catabolic and anabolic pathways to cope with environmental changes. In vitro systems, however, do not have the myriad of peripheral pathways that facilitate this control. Moreover, the natural anabolic and catabolic specificities for NADH and NADPH complicate in vitro biotransformations. Synthetic biochemistry systems have often dealt with these problems by careful considerations of cofactor stoichiometry in pathway design, through the use of expensive sacrificial metabolites, reengineering enzymes so that only a single cofactor type is needed, adding excess cofactors, or constantly adding intermediates to the reaction mix to sustain the process.

Figure 6A:
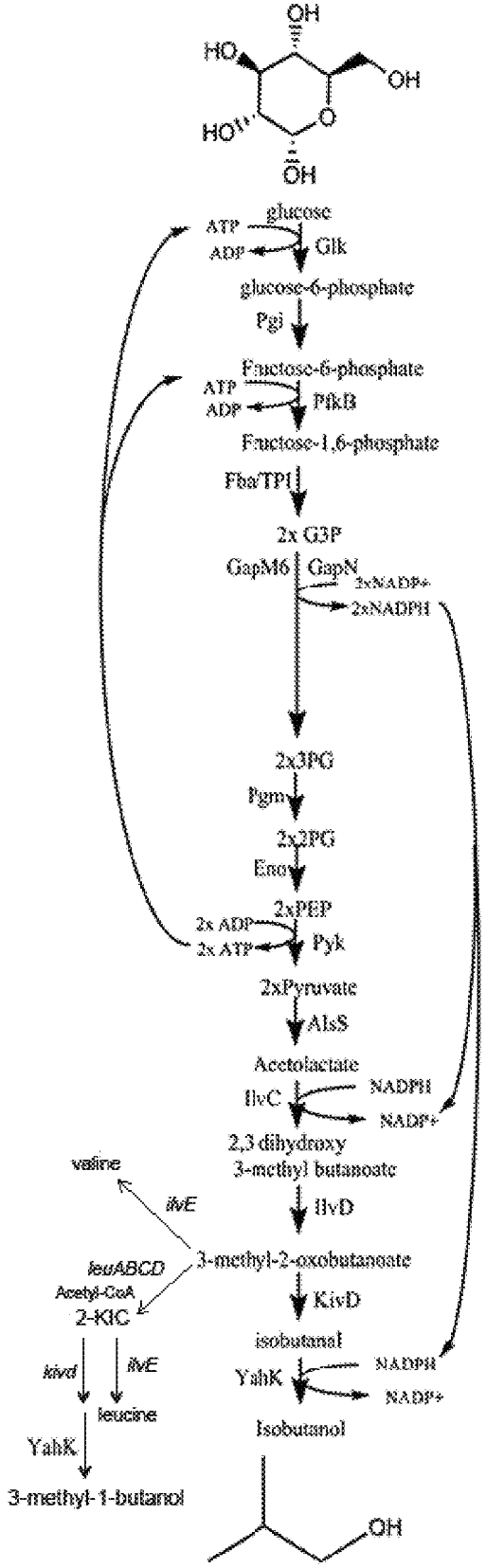
FIG. 6A-B provide detailed schematic of the stoichiometric pathway and rheostat pathway.
Figure 6B:
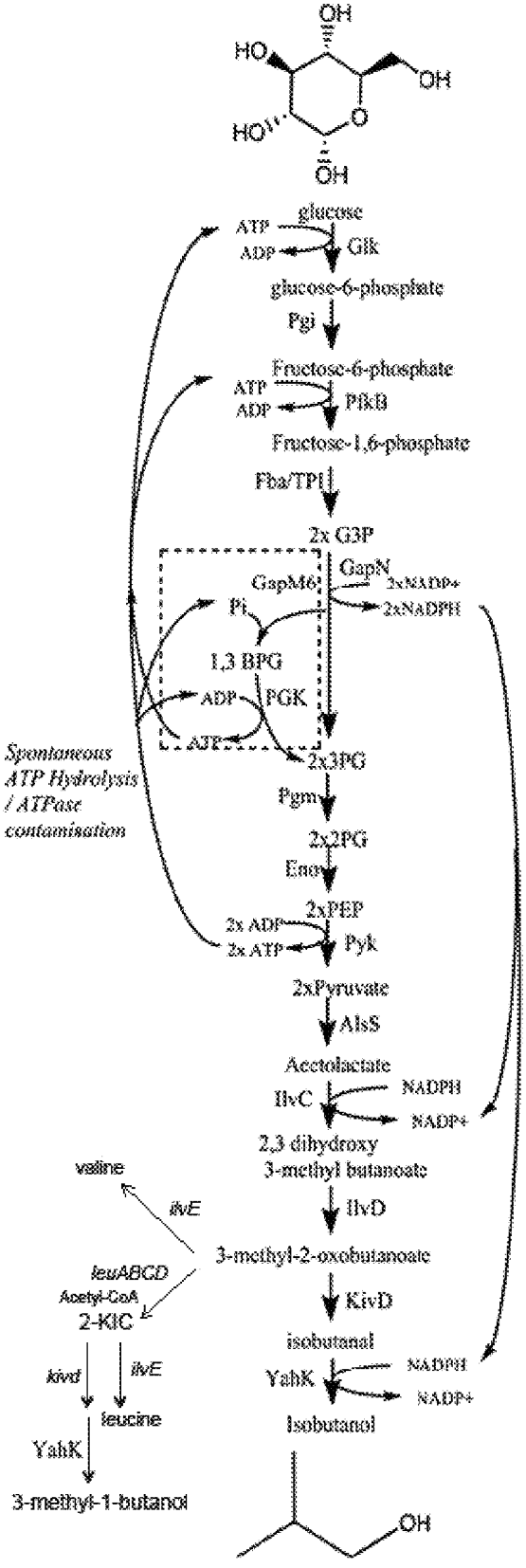
Figure 7:
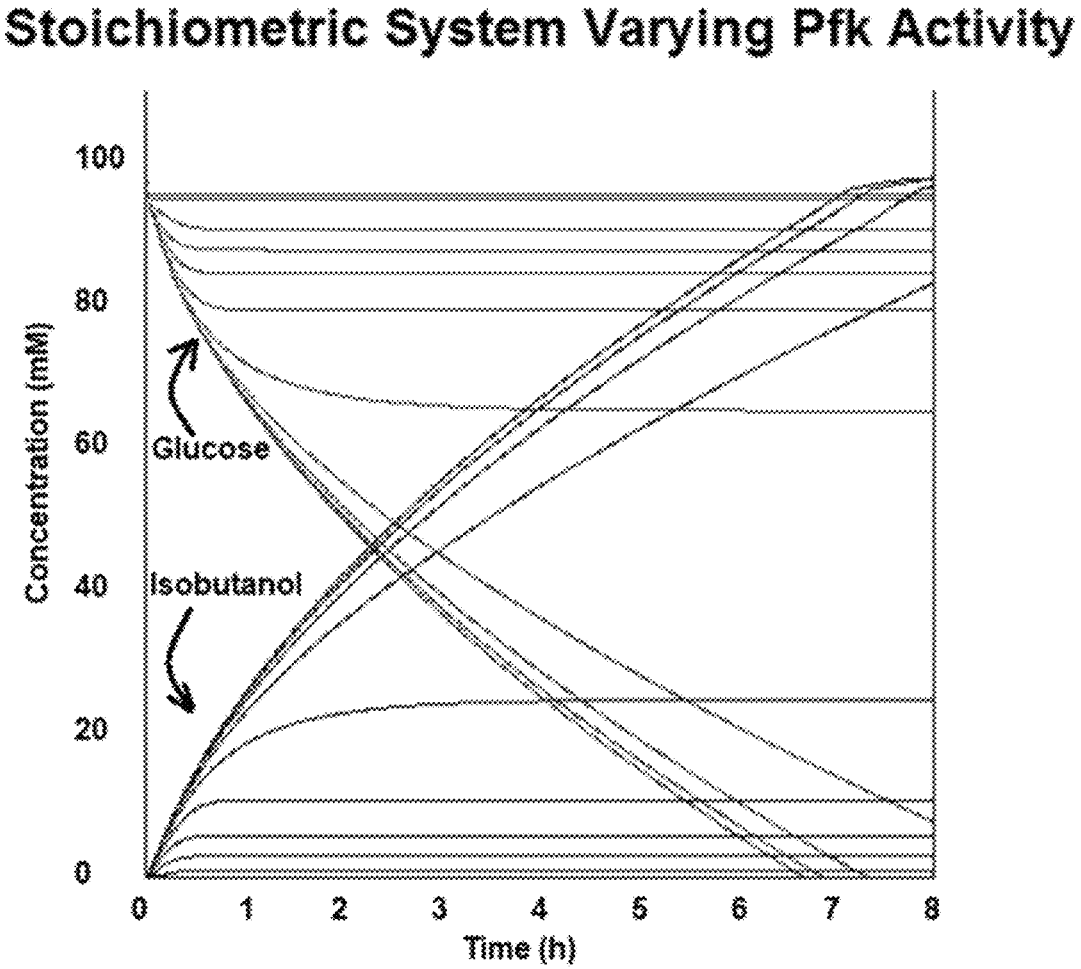
FIG. 7 provides a Caposi Model for hexokinase and the tope of glycolysis in the stoichiometric system.

Although the methods, compositions and systems described herein are described with reference to certain metabolic products, the methods, compositions and systems are applicable to a broad range of recombinant biochemical pathways where co-factor recycling is important. In one exemplary engineered pathway the disclosure describes the production of isobutanol (see, e.g., FIGS. 1, 6A and 6B).

The disclosure describes a molecular rheostat system for co-factor balance in in vitro pathways for chemical production and in vivo systems. For example, the disclosure describes a pathway to convert glucose into isobutanol that maintains sustainable reducing cofactor balance, without the requirement for perfect stoichiometric matching of cofactor generation and usage to carbon usage.

The disclosure provides a robust node of control to balance the production and consumption of cofactors such as NADPH and NADH and ATP and ADP in a self-regulating and self-balancing manner. This in vitro pathway maintains cofactor balance without requiring adherence to stoichiometry in the generation and utilization of cofactors to ensure carbon flux. In part because the system can switch between enzymatic steps based upon co-factor levels, driving the transformation to near completion.

Ultimately the methods and compositions of the disclosure can be expanded to incorporate the conversion of low cost substrates such as glucose or other sugars into useful chemicals and biofuels.

The disclosure demonstrates the design and use of a self-regulating synthetic biochemical pathways over the standard stoichiometric design using a cell free enzymatic pathway. In the production of isobutanol, the exemplary pathway described herein, the non-rheostat pathway produced about 12 g/L of isobutanol before the reaction stopped due to ATP depletion. Using the rheostat of the disclosure the system can produce an excess of ATP when needed and improved the final titer to 24 g/L.

Synthetic biochemistry systems that do not rely of perfect stoichiometry can run longer and are more flexible because cofactor stoichiometry is not constrained. The disclosure also contemplates the use of molecular purge valves in combination wih the rheotstat of the disclosure. For example, International application publication no. WO2015/153929 and International application No. PCT/US2016/043260 described such purge valve systems (the disclosure of which are incorporated herein by reference). Together, with the ATP regulatory system described here, these synthetic pathways allow for the design of self-sustaining in vitro pathways to a myriad of bio-based products that require balancing both NAD(P)/NAD(P)H and ATP individually or at the same time. These self-regulatory nodes, which can control ATP and NAD(P)/NAD(P)H, provides tools and pahways for industrial cell free enzymatic synthesis.

In one embodiment, a pathway of the disclosure provide parallel enzymatic step that utilize $NADP^+$/NADPH in a first pathway at low Pi and a second pathway that utilizes $NADP^+$/NADPH and ADP-ATP cycling at higher Pi.

The disclosure provides pathways that can be developed in vitro in a number of ways. For example, the desired enzymes can be cloned/engineered into a microorganism or cell, expressed and then purified from the culture. In another example, the enzymes can be expressed, the cells disrupted and a disrupted preparation used in the pathways of the disclosure. In another embodiment, the enzymes can be purified and tethered to a substrate in a system (e.g., in a microfluidic system) for use in the metabolic pathway. In yet another embodiment, thermophilic enzymes having the desired activity can be cloned, expressed and the cell or preparations therefrom heated to a temperature wherein the desired enzymes remain active while undesired enzymes are denatured. In yet another embodiment, the enzymes can be commercially purchased and mixed as appropriate. In all of the foregoing embodiments, the system would be combined with the necessary substrates and cofactors (e.g., $NAD^-$, $NADP^-$, $FAD^-$, AMP, ADP, ATP and the like).

Accordingly, the disclosure provides "engineered" or "modified" microorganisms that are produced via the introduction of genetic material into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite. The genetic material introduced into the parental microorganism contains gene(s), or parts of gene(s), coding for one or more of the enzymes involved in a biosynthetic pathway and include gene(s), or parts of gene(s), coding for one or more of the enzymes involved in a molecular rheostate alone or in combination with metabolic purge valve, the pathway(s) useful for the production of a desired metabolite (e.g., isobutanol), and may also include additional elements for the expression and/or regulation of expression of these genes, e.g. promoter sequences.

An engineered or modified microorganism can also include in the alternative or in addition to the introduction of a genetic material into a host or parental microorganism, the disruption, deletion or knocking out of a gene or polynucleotide to alter the cellular physiology and biochemistry of the microorganism. Through the reduction, disruption or knocking out of a gene or polynucleotide the microorganism acquires new or improved properties (e.g., the ability to produce a new or greater quantities of an intracellular metabolite, improve the flux of a metabolite down a desired pathway, and/or reduce the production of undesirable byproducts). For example, it may be desirable to engineer an organism to express a desired set for enzymes in a metabolic pathway while eliminating enzymes of competing pathways. This engineering can be applicable for both in vitro (where upon disruption or purification undesirable enzymes are not present) or in vivo.

A "native" or "wild-type" protein, enzyme, polynucleotide, gene, or cell, means a protein, enzyme, polynucleotide, gene, or cell that occurs in nature.

A "parental microorganism" refers to a cell used to generate a recombinant microorganism. The term "parental microorganism" describes, in one embodiment, a cell that occurs in nature, i.e. a "wild-type" cell that has not been genetically modified. The term "parental microorganism" further describes a cell that serves as the "parent" for further engineering. In this latter embodiment, the cell may have been genetically engineered, but serves as a source for further genetic engineering.

For example, a wild-type microorganism can be genetically modified to express or over express a first target enzyme such as a NADH-pyruvate dehydrogenase. This microorganism can act as a parental microorganism in the generation of a microorganism modified to express or over-express a second target enzyme. As used herein, "express" or "over express" refers to the phenotypic expression of a desired gene product. In one embodiment, a naturally occurring gene in the organism can be engineered such that it is linked to a heterologous promoter or regulatory domain, wherein the regulatory domain causes expression of the gene, thereby modifying its normal expression relative to the wild-type organism. Alternatively, the organism can be engineered to remove or reduce a repressor function on the gene, thereby modifying its expression. In yet another embodiment, a cassette comprising the gene sequence operably linked to a desired expression control/regulatory element is engineered in to the microorganism.

Accordingly, a parental microorganism functions as a reference cell for successive genetic modification events. Each modification event can be accomplished by introducing one or more nucleic acid molecules in to the reference cell. The introduction facilitates the expression or overexpression of one or more target enzyme or the reduction or elimination of one or more target enzymes. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of exogenous polynucleotides encoding a target enzyme in to a parental microorganism.

Polynucleotides that encode enzymes useful for generating metabolites including homologs, variants, fragments, related fusion proteins, or functional equivalents thereof, are used in recombinant nucleic acid molecules that direct the expression of such polypeptides in appropriate host cells, such as bacterial or yeast cells.

It is understood that a polynucleotide described herein include "genes" and that the nucleic acid molecules described above include "vectors" or "plasmids." Accordingly, the term "gene", also called a "structural gene" refers to a polynucleotide that codes for a particular polypeptide comprising a sequence of amino acids, which comprise all or part of one or more proteins or enzymes, and may include regulatory (non-transcribed) DNA sequences, such as promoter region or expression control elements, which determine, for example, the conditions under which the gene is expressed. The transcribed region of the gene may include untranslated regions, including introns, 5'-untranslated region (UTR), and 3'-UTR, as well as the coding sequence.

Those of skill in the art will recognize that, due to the degenerate nature of the genetic code, a variety of codons differing in their nucleotide sequences can be used to encode a given amino acid. A particular polynucleotide or gene sequence encoding a biosynthetic enzyme or polypeptide described above are referenced herein merely to illustrate an embodiment of the disclosure, and the disclosure includes polynucleotides of any sequence that encode a polypeptide comprising the same amino acid sequence of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate exemplary embodiments of the disclosure.

The disclosure provides polynucleotides in the form of recombinant DNA expression vectors or plasmids, as described in more detail elsewhere herein, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) form.

A polynucleotide of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated polynucleotide molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitution, in some positions it is preferable to make conservative amino acid substitutions.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for S. cerevisiae and mammals are UAA and UGA, respectively. The typical stop codon for monocotyledonous plants is UGA, whereas insects and E. coli commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

"Transformation" refers to the process by which a vector is introduced into a host cell. Transformation (or transduction, or transfection), can be achieved by any one of a number of means including electroporation, microinjection, biolistics (or particle bombardment-mediated delivery), or agrobacterium mediated transformation.

A "vector" generally refers to a polynucleotide that can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes,"

that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an agrobacterium or a bacterium.

The various components of an expression vector can vary widely, depending on the intended use of the vector and the host cell(s) in which the vector is intended to replicate or drive expression. Expression vector components suitable for the expression of genes and maintenance of vectors in E. coli, yeast, Streptomyces, and other commonly used cells are widely known and commercially available. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For E. coli and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433, which is incorporated herein by reference in its entirety), can also be used. For E. coli expression vectors, it is useful to include an E. coli origin of replication, such as from pUC, p1P, p1, and pBR.

Thus, recombinant expression vectors contain at least one expression system, which, in turn, is composed of at least a portion of a gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

In addition, and as mentioned above, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

In some instances "isozymes" can be used that carry out the same functional conversion/reaction, but which are so dissimilar in structure that they are typically determined to not be "homologous".

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which can also be referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used comparing a molecule sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

In certain embodiments, a metabolic pathway converts a carbon source to a desired intermediate or end product. For example, a carbon source can be converted to pyruvate, which can be metabolized to acetyl-CoA or to isobutanol. Suitable carbon sources can be sugars. For example, a carbon source can be a biomass derived sugar. A "biomass derived sugar" includes, but is not limited to, molecules such as glucose, sucrose, mannose, xylose, and arabinose. The term biomass derived sugar encompasses suitable carbon substrates of 1 to 7 carbons ordinarily used by microorganisms, such as 3-7 carbon sugars, including but not limited to glucose, lactose, sorbose, fructose, idose, galactose and mannose all in either D or L form, or a combination of 3-7 carbon sugars, such as glucose and fructose, and/or 6 carbon sugar acids including, but not limited to, 2-keto-L-gulonic acid, idonic acid (IA), gluconic acid (GA), 6-phosphogluconate, 2-keto-D-gluconic acid (2 KDG), 5-keto-D-gluconic acid, 2-ketogluconatephosphate, 2,5-diketo-L-gulonic acid, 2,3-L-diketogulonic acid, dehydroascorbic acid, erythorbic acid (EA) and D-mannonic acid.

Cellulosic and lignocellulosic feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of carbohydrate polymers comprising cellulose, hemicellulose, and lignin can be generally treated by a variety of chemical, mechanical and enzymatic means to release primarily hexose and pentose sugars. These sugars can then be "fed" into a pathway to produce pyruvate as further described herein.

The disclosure provides accession numbers for various genes, homologs and variants useful in the generation of recombinant microorganism described herein. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web.

Culture conditions suitable for the growth and maintenance of a recombinant microorganism provided herein are known in the art.

It is understood that a range of microorganisms can be engineered to express one or more enzymes of the disclosure. It is also understood that various microorganisms can act as "sources" for genetic material encoding target enzymes suitable for use in a recombinant microorganism provided herein.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the procaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt ([NaCl]); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, Micrococcus, others) (2) low G+C group (Bacillus, Clostridia, Lactobacillus, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) Bacteroides, Flavobacteria; (7) Chlamydia; (8) Green sulfur bacteria; (9) Green non-sulfur bacteria (also anaerobic phototrophs); (10) Radioresistant micrococci and relatives; and (11) Thermotoga and Thermosipho thermophiles.

"Gram-negative bacteria" include cocci, nonenteric rods, and enteric rods. The genera of Gram-negative bacteria include, for example, Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema, and Fusobacterium.

"Gram positive bacteria" include cocci, nonsporulating rods, and sporulating rods. The genera of gram positive bacteria include, for example, Actinomyces, Bacillus, Clostridium, Corynebacterium, Erysipelothrix, Lactobacillus, Listeria, Mycobacterium, Myxococcus, Nocardia, Staphylococcus, Streptococcus, and Streptomyces.

The disclosure provides a molecular rheostat for controlling ATP levels in an in vitro or in vivo system that comprises the metabolite conversion of glyceraldehyde-3-phosphate to 3-phosphoglycerate. The molecular rheostat the expression or over expression of heterologous polynucleotide or over-expression of native polynucleotides, or an enzymatic in vitro system comprising (i) an enzyme that converts glyceraldehyde-3-phosphate (G3P) and $NADP^+$ to 3-phosphoglycerate (3PG) and NADPH and (ii) an enzyme that converts glyceraldehyde-3-phosphate (G3P), $NADP^+$ and free phosphate (Pi) to 1,3-bisphosphoglycerate (1,3BPG) and (iii) an enzyme that converts 1,3 bisphosphglycerate (1,3BPG) and ADP to 3-phophoglycerate and ATP. In one embodiment, the enzyme of (i) comprises a NADP-dependent glyceraldehyde-3-phosphate dehydrogenase (GapN). In a further embodiment, the GapN is obtained from S. mutans. In another embodiment, the enzyme of (ii) comprises a mutant glyceraldehyde-3-phosphate dehydrogenase (mGap) that comprises D34A/L35R/T36K mutations relative to wild-type (SEQ ID NO:6). In another embodiment, the enzyme of (iii) comprises enzyme commission number (EC number) EC 2.7.2.3. In a further embodiment, the enzyme is a phosphoglycerate kinase. In still another embodiment, the phosphoglycerate kinase is a Pgk from G. stearothermophilus. In another embodiment, the molecular rheostat comprise the enzymes of a NADP-dependent glyceraldehyde-3-phosphate dehydrogenase (GapN), a mutant glyceraldenhyde-3-phosphate dehydrogenase that utilizes $NADP^+$ and a phosphglycerate kinase.

In another embodiment, the disclosure demonstrates the production of isobutanol using a molecular rheostat. The pathway comprises the expression or over expression of one or more heterologous polynucleotide or over-expression of one or more native polynucleotides, or an enzymatic in vitro system comprising (i) a polypeptide that catalyzes the production of glucose-6-phosphate (G6P) from glucose; (ii) a polypeptide that catalyzes the production of Fructose-6-phosphate (F6P) from glucose-6-phosphate (G6P); (iii) a polypeptide the catalyzes the conversion/phosphorylation of fructose-6-phosphate (F6P) to fructose-1,6-phosphate (iv) a polypeptide that converts fructose-1,6-phosphate to two glyceraldehyde-3-phosphates (G3P); (v) a molecular rheostat comprising (a) an enzyme that converts glyceraldehyde-3-phosphate (G3P) and $NADP^+$ to 3-phosphoglycerate (3PG) and NADPH and (b) an enzyme that converts glyceraldehyde-3-phosphate (G3P), $NADP^+$ and free phosphate (Pi) to 1,3-bisphosphoglycerate (1,3BPG) and (c) an enzyme that converts 1,3 bisphosphglycerate (1,3BPG) and ADP to 3-phophoglycerate (3pG) and ATP; (vi) a polypeptide that converts 3-phosphoglycerate (3PG) to 2-phosphoglycerate (2PG); (vii) a polypeptide that converts 2-phosphoglycerate (2PG) to phosphoenolpyruvate (PEP); (viii) a polypeptide that converts phosphoenolpyruvate (PEP) to pyruvate; (ix) a polypeptide that converts pyruvate to acetolactate; (x) a polypeptide that converts acetolactate and NADPH to 2,3 dihydroxy-3-methyl butanoate and $NADP^+$; (xi) a polypeptide that converts 2,3 dihydroxy-3-methyl butanoate to 3-methyl-2-oxobutanoate; (xii) a polypeptide that converts 3-methyl-2-oxobutanoate to isobutanal and (xiii) a polypeptide that coverts isobutanal to isobutanol.

It will be recognized by one of skill in the art that the various metabolites identified above can serve as substrate for other catabolic or anabolic pathways.

Accordingly, the disclosure provides systems and recombinant microorganisms that can produce acetyl-phosphate, pyruvate, glyceraldehyde-3-phosphate, acetyl-CoA and/or other metabolites derived therefrom wherein the system or microorganism comprises a molecular rheostat or a molecular rheostat and a purge valve. For example, the disclosure provides pathways that can comprise a molecular rheostat and one or more enzyme selected from a glucokinase (Glk or variant of homolog thereof, including a polyphosphate-dependent glucokinase, pfkA), a phosphoketolase (e.g., Fpk, Xpk, or Fpk/Xpk or variant of homolog thereof), a transaldolase (e.g., Tal or variant thereof), a transketolase (e.g., Tkt or variant of homolog thereof), ribose-5-phosphate isomerase (e.g., Rpi or variant of homolog thereof), a ribulose-5-phosphate epimerase (e.g., Rpe or variant of homolog thereof), a triose phosphate isomerase (e.g., Tpi or variant of homolog thereof), a fructose 1,6 bisphosphate aldolase (e.g., Fba or variant of homolog thereof), a phosphoglucoisomerase (e.g., Pgi or variant of homolog thereof), an enolase, a decarboxylase (e.g., KivD or homolog), an alcohol dehydrogenase (e.g., an NADPH dependent alcohol dehydrogenase such as YahK or homolog), a phosphoglucoisomerase (e.g., Pgi or homolog), a fructose 1,6 bisphosphate isomerase (Fba or homolog thereof), a phophoglycerate mutase (e.g., Pgk or homolog thereof), a pyruvate kinase (Pyk or homolog thereof), a ketol-acid reductoisomerase (IlvC or homolog thereof), a dihydroxy-acid dehydratase (e.g., IlvD or homolog thereof) and any combination thereof. Table 1 provides a list of accession number and organism that can be used as source sources of the enzymes:

TABLE 1

Enzymes and Sources:

| Enzyme | Name | Accession number | Source Organism |
|---|---|---|---|
| Sc Hk | Hexokinase | — | *S. Cerevisiae* |
| Gt PgiA | Phosphoglucoisomerase | ABO68222 | *G. thermodenitrificans* NG80-2 |

TABLE 1-continued

| Enzymes and Sources: | | | |
|---|---|---|---|
| Enzyme | Name | Accession number | Source Organism |
| Gs PfkA | Phosphoglucokinase | KOR92562 | *G. stearothermophilus* ATCC12980 |
| Sa FBA | Fructose 1,6 biphosphate aldolase | BAR10119 | *S. aureus* subsp. *Aureus* |
| Gs TPI | Triose Phosphate isomerase | KOR95273 | *G. stearothermophilus* ATCC12980 |
| Sm GapN | Non-phosphorylating Glyceraldehyde 3 phosphate dehydrogenase Phosphorylating | NP_J721104 | *S. mutans* |
| Gs mGapDH | Glyceraldehyde-3-phosphate Dehydrogenase | WP_033015082 | *G. stearothermophilus* ATCC12980 |
| Gs PGK | Phophoglycerate Kinase | WP_033015089 | *G. stearothermophilus* ATCC12980 |
| Gs PGM | Phosphoglycerate Mutase | KOR95274 | *G. stearothermophilus* ATCC12980 |
| Ec Enolase | Enolase | NP_417259 | *E. coli* K12 sp MG1655 |
| Ec PykF | Pyruvate Kinase | NP_416191 | *E. coli* K12 sp MG1655 |
| Bs AlsS | Acetolactate Synthase | NP_391482 | *B. Subtilis subtilis* 168 |
| Ec IlvC | Ketol-Acid Reductoisomerase | AKK14493 | *E. coli* K12 sp MG1655 |
| Re IlvD | Dihydroxy-Acid Dehydratase | Q0K4J3 | *R. eutropha* |
| Ll KlvD | Keto-Isovalerate Decarboxylase | CAG34226 | *L. lactis* subsp. *Lactis* |
| Ec YahK | Alcohol Dehydrogenase | NC_000913.3 | *E. coli* K12 |

The foregoing one or more enzymes can be used in combination with enzymes that catalyze the conversion of glyceraldehyde-3-phosphate to 3-phosphoglycerate with or without an intermediate step of conversion to 1,3-bisphosphoglycerate, wherein the intermediate step is regulated by the level of phosphate.

In addition, a microorganism may include a disruption, deletion or knockout of expression of an alcohol/acetoaldehyde dehydrogenase that preferentially uses acetyl-coA as a substrate (e.g. adhE gene), as compared to a parental microorganism. In some embodiments, further knockouts may include knockouts in a lactate dehydrogenase (e.g., ldh) and frdBC. In other embodiments, knockouts or reductions in expression or activity of one or more of gapA, eda, edd and mgsA may be performed to remove other glycolysis pathways in the microorganism. Other enzymes that can be knocked out or expression reduced include Fbp, glpX, and homologs and variants thereof.

It will be recognized that subsystems or organism that have one or more (but not all) of the foregoing enzymes can be utilized and then combined with an organism or other subsystems comprising remaining enzymatic members of the pathway.

As previously noted, the target enzymes described throughout this disclosure generally produce metabolites. In addition, the target enzymes described throughout this disclosure are encoded by polynucleotides.

Accordingly, in one embodiment, a system or recombinant microorganism provided herein comprises a glucokinase (Glk, polyphosphate-dependent glucokinase or homolog or variant thereof). This expression may be combined with enzymes of the molecular rheostat and may further include additional downstream enzymes for the production of a desired metabolite. The Glk can be derived from G. stearothermophilus. In another embodiment, an engineered variant of Glk can be used so long as it has glucokinase activity and can convert glucose to glucose-6-phosphate. Such engineered variants can be obtained by site-directed mutagenesis, directed evolutions and the like. Thus included within the disclosure are polypeptides that are at least 85-99% identical to the sequence of Glk from E. coli and having glucokinase activity.

In another or further embodiment, a system or recombinant microorganism provided herein includes expression of a phosphofructokinase (Pfk, polyphosphate-dependent Pfk or homolog or variants thereof). This expression may be combined with other enzymes in the metabolic pathway for the production of acetyl-phosphate, acetyl-coA or other metabolites derived therefrom. The Pfk can be derived from G. stearothermophilus. In another embodiment, an engineered variant of Pfk can be used so long as it has phosphoglucokinase and/or phosphofructokinase activity and can convert fructose-6 phosphate to fructose-1,6-phosphate. Such engineered variants can be obtained by site-directed mutagenesis, directed evolutions and the like. Thus included within the disclosure are polypeptides that are at least 85-99% identical to a sequence Pfk from G. sterothermophilus and having 6-phosphofructokinase activity (e.g., 85-100% identical to SEQ ID NO:1).

In another embodiment, a system or recombinant microorganism provided herein includes a triose phosphate isomerase. This enzyme may be combined with other enzymes in the metabolic pathway for the production of acetyl-phosphate, pyruvate, acetyl-CoA or other metabolites derived therefrom as described herein above and below. The enzyme produces a metabolite that includes glyceraldehyde-3-phosphate from fructose-1,6-phosphate. The triose phosphate isomerase can be encoded by a Tpi gene, polynucleotide or homolog thereof. The Tpi gene or polynucleotide can be derived from various microorganisms including G. stearothermophilus and E. coli.

In addition to the foregoing, the terms "triose phosphate isomerase" or "Tpi" refer to proteins that are capable of catalyzing the formation of glyceraldehyde-3-phosphate from fructose-1,6-phosphate, and which share at least about 40%, 45%, 50%, 55%, 60%, 65%, 70%, 75%, 80%, 85%, 90%, 95%, 96%, 97%, 98%, 99% or greater sequence identity to SEQ ID NO:2, or at least about 50%, 60%, 70%, 80%, 90%, 95%, 96%, 97%, 98%, 99% or greater sequence similarity, as calculated by NCBI BLAST, using default parameters. Additional homologs include: G. stearothermophilus ATCC12980, KOR95273 (SEQ ID NO:2); Rattus norvegicus AAA42278.1; Homo sapiens AAH17917.1; Bacillus subtilis BEST7613 NP 391272.1; Synechococcus elongatus PCC 6301 YP 171000.1; and Salmonella enterica subsp. enterica serovar Typhi str. AG3 ZP_06540375.1. The sequences associated with the foregoing accession numbers are incorporated herein by reference.

In another embodiment, a system or recombinant microorganism provided herein includes a fructose 1,6 bisphosphate aldolase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes glyceraldeyde-3-phosphate from fructose 1,6-bisphosphate. The fructose 1,6 bisphosphate aldolase can be encoded by a Fba gene, polynucleotide or homolog thereof. The Fba gene or polynucleotide can be derived from various microorganisms including S. aureus.

In addition to the foregoing, the terms "fructose 1,6 bisphosphate aldolase" or "Fba" refer to proteins that are capable of catalyzing the formation of glyceraldehyde-3-phosphate from fructose 1,6-bisphosphate, and which share at least about 40%, 45%, 50%, 55%, 60%, 65%, 70%, 75%, 80%, 85%, 90%, 95%, 96%, 97%, 98%, 99% or greater sequence identity to SEQ ID NO:3, or at least about 50%, 60%, 70%, 80%, 90%, 95%, 96%, 97%, 98%, 99% or greater sequence similarity, as calculated by NCBI BLAST, using default parameters. Additional homologs include: S. aureus subsp. Aureus, BAR10119 (SEQ ID NO:3); Synechococcus elongatus PCC 6301 YP_170823.1; Vibrio nigripulchritudo ATCC 27043 ZP_08732298.1; Methylomicrobium album BG8 ZP_09865128.1; Pseudomonas fluorescens Pf0-1 YP_350990.1; and Methylobacterium nodulans ORS 2060 YP_002502325.1. The sequences associated with the foregoing accession numbers are incorporated herein by reference.

In another embodiment, a system or recombinant microorganism provided herein includes a phosphoglucoisomerase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes fructose-phosphate from glucose-6-phosphate. The phosphoglucokinase can be encoded by a Pgi gene, polynucleotide or homolog thereof. The Pgi gene or polynucleotide can be derived from various microorganisms including G. thermodenitrificans.

In addition to the foregoing, the terms "phosphoglucoisomerase" or "Pgi" refer to proteins that are capable of catalyzing the formation of fructose-6-phosphate from glucose-6-phosphate, and which share at least about 40%, 45%, 50%, 55%, 60%, 65%, 70%, 75%, 80%, 85%, 90%, 95%, 96%, 97%, 98%, 99% or greater sequence identity to SEQ ID NO:4, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes a non-phosphorylating glyceraldehyde-3-phosphate dehydrogenase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes 3-phosphoglycerate from glyceraldehyde-3-phosphate. The non-phosphorylating glyceraldehyde-3-phosphate dehydrogenase can be encoded by a GapN gene, polynucleotide or homolog thereof. The GapN gene or polynucleotide can be derived from various microorganisms including S. mutans.

In addition to the foregoing, the terms "non-phosphorylating glyceraldehyde-3-phosphate dehydrogenase" or "GapN" refer to proteins that are capable of catalyzing the formation of 3-phosphoglycerate from glyceraldehyde-3-phosphate, and which share at least about 40%, 45%, 50%, 55%, 60%, 65%, 70%, 75%, 80%, 85%, 90%, 95%, 96%, 97%, 98%, 99% or greater sequence identity to SEQ ID NO:5, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes a mutant phophorylating glyceraldehyde-3-phosphate dehydrogenase the preferentially used $NADP^+$. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes 1,3-bisphosphoglycerate from glyceraldehyde-3-phosphate. The mutant phophorylating glyceraldehyde-3-phosphate dehydrogenase can be encoded by mutated from a GapDH gene, polynucleotide or homolog thereof to include mutations D34A/L35R/T36K. The GapDH gene or polynucleotide can be derived from various microorganisms including G. stearothermophilus.

In addition to the foregoing, the terms "mutant phophorylating glyceraldehyde-3-phosphate dehydrogenase" or "mGap" refer to proteins that are capable of catalyzing the formation of 1,3-bisphosphoglycerate from glyceraldehyde-3-phosphate and NADP+ and free phosphate (Pi), and which share at least about 40%, 45%, 50%, 55%, 60%, 65%, 70%, 75%, 80%, 85%, 90%, 95%, 96%, 97%, 98%, 99% or greater sequence identity to SEQ ID NO:6 and includes the mutations D34A/L35R/T36K, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes a phosphoglycerate kinase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes 3-phosphoglycerate from 1,3-bisphosphoglycerate and ADP. The phosphoglycerate kinase can be encoded by a Pgk gene, polynucleotide or homolog thereof. The Pgk gene or polynucleotide can be derived from various microorganisms including G. stearothermophilus.

In addition to the foregoing, the terms "phosphoglycerate kinase" or "Pgk" refer to proteins that are capable of catalyzing the formation of 3-phosphoglycerate from 1,3-bisphosphoglycerate and ADP, and which share at least about 40%, 45%, 50%, 55%, 60%, 65%, 70%, 75%, 80%, 85%, 90%, 95%, 96%, 97%, 98%, 99% or greater sequence identity to SEQ ID NO:7, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes a phosphoglycerate mutase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes 2-phosphoglycerate from 3-phosphoglycerate. The phosphoglycerate mutase can be encoded by a Pgm gene, polynucleotide or homolog thereof. The Pgm gene or polynucleotide can be derived from various microorganisms including G. stearothermophilus.

In addition to the foregoing, the terms "phosphoglycerate mutase" or "Pgm" refer to proteins that are capable of catalyzing the formation of 2-phosphoglycerate from 3-phosphoglycerate, and which share at least about 40%, 45%, 50%, 55%, 60%, 65%, 70%, 75%, 80%, 85%, 90%, 95%, 96%, 97%, 98%, 99% or greater sequence identity to SEQ ID NO:8, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes an enolase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes phosphoenolpyruvate from 2-phosphoglycerate. The enolase can be encoded by an enolase gene, polynucleotide or homolog thereof. The enolase gene or polynucleotide can be derived from various microorganisms including E. coli.

In addition to the foregoing, the terms "enolase" refer to proteins that are capable of catalyzing the formation of phospoenolpyruvate from 2-phosphoglycerate, and which share at least about 40%, 45%, 50%, 55%, 60%, 65%, 70%, 75%, 80%, 85%, 90%, 95%, 96%, 97%, 98%, 99% or greater sequence identity to SEQ ID NO:9, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes a pyruvate kinase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes pyruvate from phosphoenolpyruvate. The pyruvate kinase can be encoded by a Pyk gene, polynucleotide or homolog thereof. The Pyk gene or polynucleotide can be derived from various microorganisms including E. coli.

In addition to the foregoing, the terms "pyruvate kinase" or "Pyk" refer to proteins that are capable of catalyzing the formation of pyruvate from phosphoenolpyruvate, and which share at least about 40%, 45%, 50%, 55%, 60%, 65%, 70%, 75%, 80%, 85%, 90%, 95%, 96%, 97%, 98%, 99% or greater sequence identity to SEQ ID NO:10, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes an acetolactate synthase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes acetolactate from pyruvate. The acetolactate synthase can be encoded by a AlsS gene, polynucleotide or homolog thereof. The AlsS gene or polynucleotide can be derived from various microorganisms including B. subtilis. In one aspect, the acetohydroxy acid synthase may be encoded by a polynucleotide derived from the ilvIH operon, ilvBN operon, ilvGM in E. coli, or the alsS gene from Bacillus subtilis, or homologs thereof. The ilvI gene of the ilvIH operon encodes an acetohydroxyacid synthase large subunit polypeptide and the ilvH gene of the ilvIH operon encodes an acetohydroxyacid synthase small subunit polypeptide.

In addition to the foregoing, the terms "acetolactate synthase" or "AlsS" refer to proteins that are capable of catalyzing the formation of pyruvate from phosphoenolpyruvate, and which share at least about 40%, 45%, 50%, 55%, 60%, 65%, 70%, 75%, 80%, 85%, 90%, 95%, 96%, 97%, 98%, 99% or greater sequence identity to SEQ ID NO:11, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes an acetohydroxy acid isomeroreductase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes 2,3 dihydroxy-3-methyl butanoate from acetolactate. The acetohydroxy acid isomeroreductase can be encoded by a IlvC gene, polynucleotide or homolog thereof. The IlvC gene or polynucleotide can be derived from various microorganisms including E. coli. Acetohydroxy acid isomeroreductase is the second enzyme in parallel pathways for the biosynthesis of isoleucine and valine. IlvC encodes an acetohydroxy acid isomeroreductase in E. coli. Homologs and variants of ilvC are known and include, for example, acetohydroxyacid reductoisomerase (Schizosaccharomyces pombe 972h−) gi|162312317|ref|NP_001018845.2|(162312317); acetohydroxyacid reductoisomerase (Schizosaccharomyces pombe) gi|3116142|emb|CAA18891.1|(3116142); acetohydroxyacid reductoisomerase (Saccharomyces cerevisiae YJM789) gi|151940879|gb|EDN59261.1|(151940879); Ilv5p: acetohydroxyacid reductoisomerase (Saccharomyces cerevisiae) gi|609403|gb|AAB67753.1|(609403); ACL198Wp (Ashbya gossypii ATCC 10895) gi|45185490|ref|NP_983206.1|(45185490); ACL198Wp (Ashbya gossypii ATCC 10895) gi|44981208|gb|AAS51030.1|(44981208); acetohydroxyacid isomeroreductase; Ilv5x (Saccharomyces cerevisiae) gi|957238|gb|AAB33579.1||bbm|369068|bbs|165406 (957238); acetohydroxy-acid isomeroreductase; Ilv5g (Saccharomyces cerevisiae) gi|957236|gb|AAB33578.1||bbm|369064|bbs|165405 (957236); and ketol-acid reductoisomerase (Schizosaccharomyces pombe) gi|2696654|dbj|BAA24000.1|(2696654), each sequence associated with the accession number is incorporated herein by reference.

In addition to the foregoing, the terms "acetohydroxy acid isomeroreductase" or "IlvC" refer to proteins that are capable of catalyzing the formation of pyruvate from phosphoenolpyruvate, and which share at least about 40%, 45%, 50%, 55%, 60%, 65%, 70%, 75%, 80%, 85%, 90%, 95%, 96%, 97%, 98%, 99% or greater sequence identity to SEQ ID NO:12, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes dihydroxy-acid dehydratase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes 3-methyl-2-oxobutanoate from 2,3 dihydroxy-3-methyl butanoate. The dihydroxy-acid dehydratase can be encoded by a IlvD gene, polynucleotide or homolog thereof. The IlvD gene or polynucleotide can be derived from various microorganisms including E. coli. Dihydroxy-acid dehydratases catalyzes the fourth step in the biosynthesis of isoleucine and valine, the dehydratation of 2,3-dihydroxy-isovaleic acid into alpha-ketoisovaleric acid. IlvD and ilv3 encode a dihydroxy-acid dehydratase. Homologs and variants of dihydroxy-acid dehydratases are known and include, for example, IlvD (Mycobacterium leprae) gi|2104594|emb|CAB08798.1|(2104594); dihydroxy-acid dehydratase (Tropheryma whipplei TW08/27) gi|28410848|emb|CAD67234.1|(28410848); dihydroxy-acid dehydratase (Mycobacterium leprae) gi|13093837|emb|CAC32140.1|(13093837); dihydroxy-acid dehydratase (Rhodopirellula baltica SH 1) gi|32447871|emb|CAD77389.1|(32447871); and putative dihydroxy-acid dehydratase (Staphylococcus aureus subsp. aureus MRSA252) gi|49242408|emb|CAG41121.1| (49242408), each sequence associated with the accession numbers are incorporated herein by reference.

In addition to the foregoing, the terms "dihydroxy-acid dehydratase" or "IlvD" refer to proteins that are capable of catalyzing the formation of pyruvate from phosphoenolpyruvate, and which share at least about 40%, 45%, 50%, 55%, 60%, 65%, 70%, 75%, 80%, 85%, 90%, 95%, 96%, 97%, 98%, 99% or greater sequence identity to SEQ ID NO:13, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes 2-ketoacid decarboxylase (also referred to as a keto-isovalerate decarboxylase). This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes isobutanal from 3-methyl-2-oxobutanoate. The 2-ketoacid decarboxylase can be encoded by a kivD gene, polynucleotide or homolog thereof. The kivD gene or polynucleotide can be derived from various microorganisms including L. lactis. Dihydroxy-acid dehydratases catalyzes the fourth step in the biosynthesis of isoleucine and valine, the dehydratation of 2,3-dihydroxy-isovaleic acid into alpha-ketoisovaleric acid. IlvD and ilv3 encode a dihydroxy-acid dehydratase. 2-ketoacid decarboxylases catalyze the conversion of a 2-ketoacid to the respective aldehyde. For example, 2-ketoisovalerate decarboxylase catalyzes the conversion of 2-ketoisovalerate to isobutyraldehyde. A number of 2-ketoacid decarboxylases are known and are exemplified by the pdc, pdc1, pdc5, pdc6, aro10, thI3, kdcA and kivd genes. Exemplary homologs and variants useful for the conversion of a 2-ketoacid to the respective aldehyde comprise sequences designated by the following accession numbers and identified enzymatic activity: gi|44921617|gb|AAS49166.1| branched-chain alpha-keto acid decarboxylase (Lactococcus lactis); gi|15004729|ref|NP_149189.1| Pyruvate decarboxylase (Clostridium acetobutylicum ATCC 824); gi|82749898|ref|YP_415639.1| probable pyruvate decarboxylase (Staphylococcus aureus RF122); gi|77961217|ref|ZP_00825060.1| COG3961: Pyruvate decarboxylase and related thiamine pyrophosphate-requiring enzymes (Yersinia mollaretii ATCC 43969); gi|71065418|ref|YP_264145.1| putative pyruvate decarboxylase (Psychrobacter arcticus 273-4); gi|16761331|ref|NP_456948.1| putative decarboxylase (Salmonella enterica subsp. enterica serovar Typhi str. CT18); gi|93005792|ref|YP_580229.11 Pyruvate decarboxylase (Psychrobacter cryohalolentis K5); gi|23129016|ref|ZP_00110850.1| COG3961: Pyruvate decarboxylase and related thiamine pyrophosphate-requiring enzymes (Nostoc punctiforme PCC 73102); gi|16417060|gb|AAL18557.1|AF354297_1 pyruvate decarboxylase (Sarcina ventriculi); gi|15607993|ref|NP_215368.1|PROBABLE PYRUVATE OR INDOLE-3-PYRUVATE DECARBOXYLASE PDC (Mycobacterium tuberculosis H37Rv); gi|41406881|ref|NP_959717.1| Pdc (Mycobacterium avium subsp. paratuberculosis K-10); gi|91779968|ref|YP_555176.1| putative pyruvate decarboxylase (Burkholderia xenovorans LB400); gi|15828161|ref|NP_302424.1| pyruvate (or indolepyruvate) decarboxylase (Mycobacterium leprae TN); gi|118616174|ref|YP 904506.1| pyruvate or indole-3-pyruvate decarboxylase Pdc (Mycobacterium ulcerans Agy99); gi|67989660|ref|NP_001018185.1| hypothetical protein SPAC3H8.01 (Schizosaccharomyces pombe 972h−); gi|21666011IgbIAAM73540.1|AF282847_1 pyruvate decarboxylase PdcB (Rhizopus oryzae); gi|69291130|ref|ZP_00619161.1| Pyruvate decarboxylase: Pyruvate decarboxylase (Kineococcus radiotolerans SRS30216); gi|66363022|ref|XP_628477.1| pyruvate decarboxylase (Cryptosporidium parvum Iowa II); gi|70981398|ref|XP_731481.1| pyruvate decarboxylase (Aspergillus fumigatus Af293); gi|121704274|ref|XP_001270401.1| pyruvate decarboxylase, putative (Aspergillus clavatus NRRL 1); gi|119467089|ref|XP_001257351.1| pyruvate decarboxylase, putative (Neosartorya fischeri NRRL 181); gi|26554143|ref|NP_758077.1| pyruvate decarboxylase (Mycoplasma penetrans HF-2); gi|21666009|gb|AAM73539.1|AF282846_1 pyruvate decarboxylase PdcA (Rhizopus oryzae) each sequence associated with the accession numbers are incorporated herein by reference.

The 2-keto acid decarboxylase activity can be provided by one of the following genes: PDC6 from Saccharomyces cerevisiae, kivd from Lactococcus lactis, and THIS Saccharomyces cerevisiae (α-ketoisocaproate decarboxylase) and pdc Clostridium acetobutylicum. The alcohol dehydrogenase (Adh) activity can be provided by ADH2 from Saccharomyces cerevisiae.

In addition to the foregoing, the terms "2-ketoacid decarboxylase" or "kivD" refer to proteins that are capable of catalyzing the formation of pyruvate from phosphoenolpyruvate, and which share at least about 40%, 45%, 50%, 55%, 60%, 65%, 70%, 75%, 80%, 85%, 90%, 95%, 96%, 97%, 98%, 99% or greater sequence identity to SEQ ID NO:14, or at least about 50%, 60%, 70%, 80%, 90%, 95%, 96%, 97%, 98%, 99% or greater sequence similarity, as calculated by NCBI BLAST, using default parameters.

In another embodiment, a system or recombinant microorganism provided herein includes an alcohol dehydrogenase. This enzyme may be combined with the expression or over-expression with other enzymes in the metabolic pathway for the production of acetyl-phosphate, acetyl-CoA or other metabolites derived therefrom as described herein above and below. The enzyme produces a metabolite that includes isobutanol from isobutanal. The alcohol dehydrogenase can be encoded by a Yahk gene, polynucleotide or homolog thereof. The Yahk gene or polynucleotide can be derived from various microorganisms including E. coli.

In addition to the foregoing, the terms "alcohol dehydrogenase" or "Yahk" refer to proteins that are capable of catalyzing the formation of pyruvate from phosphoenolpyruvate, and which share at least about 40%, 45%, 50%, 55%, 60%, 65%, 70%, 75%, 80%, 85%, 90%, 95%, 96%, 97%, 98%, 99% or greater sequence identity to SEQ ID NO:15, or at least about 50%, 60%, 70%, 80%, 90%, 95%, 96%, 97%, 98%, 99% or greater sequence similarity, as calculated by NCBI BLAST, using default parameters.

In all of the foregoing embodiments, a system or recombinant microorganism provided herein may include a purge valve. The purge valve includes an enzymatic reaction the vents/removes or otherwise eliminates over abundance of an excessive co-factor in order to maintain system function. For example, in one embodiment, the purge valve includes an NADH-oxidase (NoxE). The NADH oxidase can be encoded by a NoxE gene, polynucleotide or homolog thereof. The NoxE gene or polynucleotide can be derived from various microorganisms including L. lactis (see, e.g., Accession number YP_007507681).

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"), each of which is incorporated herein by reference in its entirety.

Examples of protocols sufficient to direct persons of skill through in vitro amplification methods, including the polymerase chain reaction (PCR), the ligase chain reaction (LCR), 0-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13:563-564.

Improved methods for cloning in vitro amplified nucleic acids are described in Wallace et al., U.S. Pat. No. 5,426,039.

Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The invention is illustrated in the following examples, which are provided by way of illustration and are not intended to be limiting.

EXAMPLES

Miller LB media or Miller LB-agar (BD Difco) was used for growth of bacterial strains in liquid or solid media. E. coli BL21Gold(DE3) [B, F−, ompT, hsdS$_B$, ($r_B$−,$m_B$−), dcm+, Tet$^r$, galλ, (DE3) endA Hte] (Agilent) was used as host for both cloning and expression of recombinant proteins using pET vectors. E. coli TOP10(DE3) [F− mcrA Δ(mrr-hsdRMS-mcrBC) Ψ801 acZΔM15 ΔlacX74 nupG recA1 araD139 Δ(ara-leu)7697 galE15 galK16 rpsL(Str$^R$) endA1 λ$^-$] was used for expression of recombinant proteins from the pBAD/p15A vector. Plasmids pET28a(+) and pET22b (+) were purchased from Novagen. HotStart Taq Mastermix (Denville) was used for gene amplification from genomic or plasmid DNA. Phusion DNA polymerase (Finnizymes), Taq DNA ligase (MCLab), and T5 Exonuclease (Epicenter) were purchased separately and used to make the assembly master mix (AMM) used for cloning. ATP, pyruvate, and NAD(P)' were from Sigma.

Plasmid Construction.

The expression plasmids for the enzymes were constructed from the pET28a plasmid backbone using the Nde1 and Sac1 cut sites to produce constructs with an N-terminal 6×His tag for purification. E. coli BL21-Gold cells were used as the host strain for enzyme expression. All enzymes were expressed in Luria-Bertani (LB) media supplemented with 50 μg/mL kanamycin and were induced with 0.2 mM isopropyl-β-D-1-thioglactopyranoside added to the culture at the end of log phase growth.

Enzyme Purification.

Cells from 0.5 L of culture were harvested by centrifugation and resuspended in 150 mM Tris pH 7.5, 100 mM NaCl. The cells were lysed on ice with sonication and the cell debris was removed by 12,000×g centrifugation at 4° C. The supernatant was then mixed with 5 mL nickel-nitrilotriacetic acid (NTA) agarose and after 30 minutes, the agarose slurry was loaded onto a gravity column and washed with five column volumes of 100 mM Tris pH 7.5, 100 mM NaCl, 15 mM imidazole. The enzyme was then eluted with 250 mM imidazole, 100 mM Tris pH 7.5. The resulting enzyme was dialyzed into 50 mM Tris pH 7.5, 50 mM NaCl and stored at 4° C.

Enzyme activity and optimization. All of the enzymes used in this work were assayed. The enzymes were assayed in 50 mM tris buffer pH 7.5, 5 mM MgCl, and 5 mM KCl which mirrors the final reaction conditions. The activity of NAD(P)H producing or consuming reactions were monitored at 340 nm. The activity of ATP consuming enzymes were monitored using a coupled assay with Zwf and $NADP^+$ at 340 nm.

ATPase assays of the enzymes were tested with 5 mM PEP, 1 mM ATP, 1 ul PK/LDH, 0.25 mM NADH and 5 ul of the given enzyme. The ATPase activity was calculated by the decrease in NADH concentration at 340 nm.

Final Isobutanol Reaction Conditions and Analysis.

The optimized self-sustaining reaction for the biotransformation glucose to isobutanol composed of 50 mM Tris pH 7.5, 5 mM MgCl, 5 mM KCl, 2 mM $NADP^+$, 4 mM ATP, 1 mM glutathione, 0.25 mM TPP, 0.25 mM MnCl, 4 mM Pi, 0.5 mM 2,3 BPG, and 660 mM glucose in a final reaction volume of 200 μL. The reactions were initiated with the addition of glucose, which was left out of the initial mixture. All reactions were performed at room temperature.

To assay for isobutanol, the reactions were incubated and extracted with 0.3 mL hexanes. 1 ul of the hexane layer was applied to a 0.25 micron HP-Innowax column using a HP 5890 Series II gas chromatogram. The GC method used an injection temperature that was held at 50° C. for 5 minutes before it was increased to 275° C. over 35 minutes. The peak intensities were compared to an authentic standard to assess concentrations.

A Stoichiometric Isobutanol Pathway.

A pathway was designed and implemented to make isobutanol with stoichiometric recycling of high energy cofactors. The 2-keto-acid isobutanol build phase employs 2 pyruvate and 2 NADPH, but no ATP, whereas the canonical glycolysis pathway produces 2 pyruvate, 2 NADH and 2 ATP. Thus to make the cofactor use stoichiometric the pathway needed (1) generate 2 NADPH rather than NADH and (2) eliminate net ATP production. With these constraints in mind, the 14 enzyme pathway shown in FIGS. 1 and 6 was developed in which glyceraldehyde phosphate dehydrogenase (GAPDH) and phosphoglycerate kinase (PGK) are replaced with a non-phosphorylating glyceraldehyde phosphate dehydrogenase (GAPN). The use of GAPN eliminates the production of 2 ATP and generates NADPH rather than NADH. The overall pathway becomes stoichiometric with respect to the production and consumption of both ATP and NADPH and has an overall theoretical carbon yield of 41%.

Figure 2A:
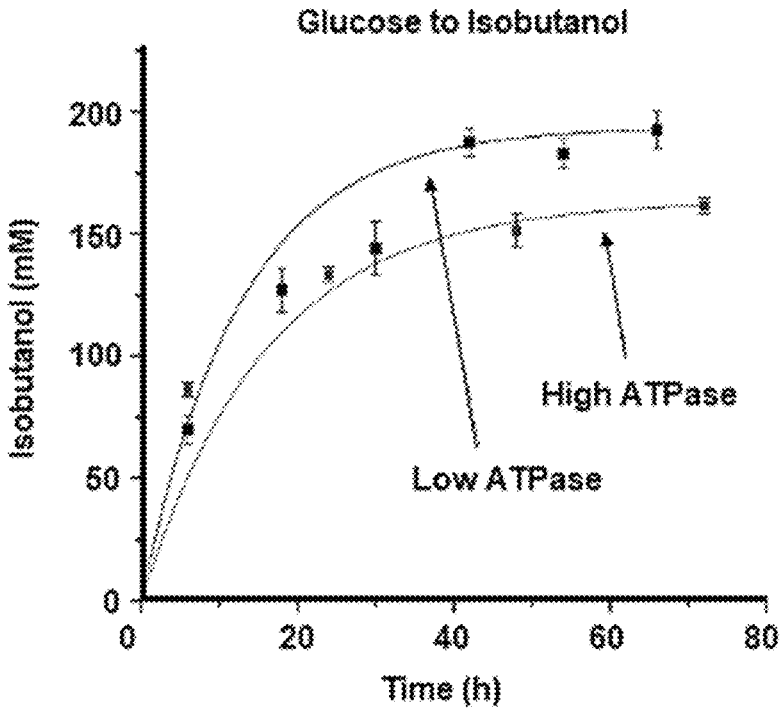
FIG. 2A-B shows results of the stoichiometric pathway from glucose to isobutanol. (A) Time course production from the stoichiometric pathway using a fully purified system. The initial time course production had a high amount of ATPase contamination and produced 11.96±1.57 g/L. The second time course had a lower amount of ATPase activity which increased the isobutanol production to 14.26±0.57 g/L. (B) Histogram of isobutanol production from the stoichiometric pathway after 48 hours after NADPH or ATP supplementation at 24 hours.

The overall pathway shown in FIG. 1 was first modeled using COPASI to identify likely key steps in the pathway. The model revealed that the relative activities of hexokinase and phosphofructokinase were useful for achieving flux through the system. The result makes sense because in glycolysis, hexokinase and phosphofructokinse compete with each other for any available ATP. Therefore, when the relative activity of hexokinase is too high, ATP can be rapidly exhausted in the production glucose-6-phosphate (G6P) leaving insufficient ATP for the phosphofructokinase reaction, ultimately stopping the carbon flux and killing the reaction. With this in mind, initial reactions were set up with hexokinase as the limiting enzyme. Once isobutanol production from glucose was detected, cofactor and enzyme concentrations were systematically optimized, resulting in the production time course seen in FIG. 2A. The high initial productivity sharply decreased by 18 hours rising to a titer of 161±3 mM isobutanol after 3 days (11.9±0.2 g/L).

As the pathway is stoichiometrically balanced with respect to ATP production and consumption, it was speculated that the sharp decrease in reaction rate might be due to ATPase activity in the system. Accordingly, ATPase activity was measure in each of the individual enzymes in the pathway and found that the enolase and ilvC enzyme preparations possessed notably higher ATPase levels than the other enzymes in the system. Accordingly, enolase and ilvC were repurified, which reduced contaminating ATPase activity. The stoichiometric reaction was set up again with the repurified enzymes, leading to an improved titer of 192±8 mM isobutanol over the course of three days (14.2±0.6 g/L). Nevertheless, production still decreased after 18 hours.

Figure 2B:
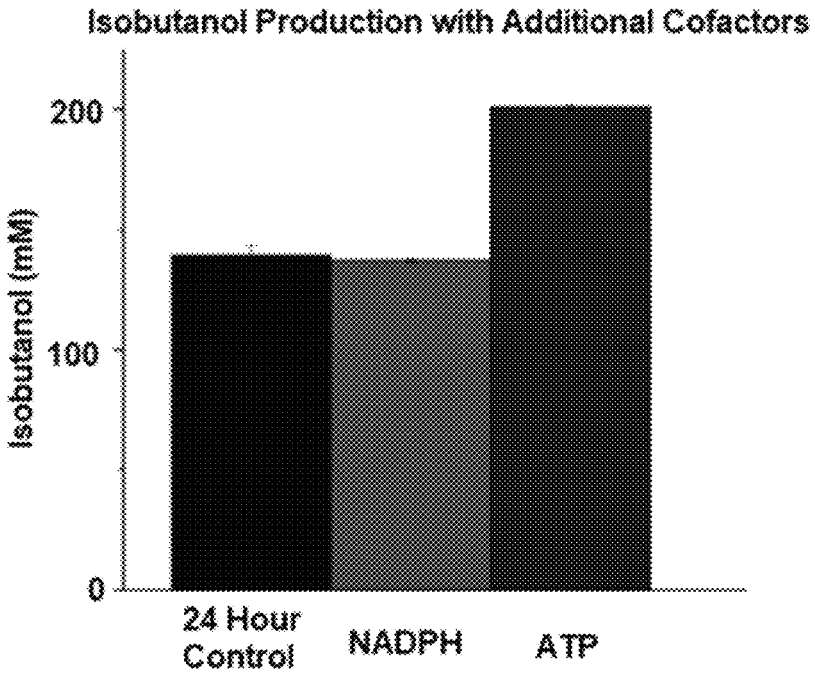

Test were performed to analyze if cofactor depletion remained a problem by initiating the reactions as usual and then adding another bolus of ATP or NADPH after 24 hours (FIG. 2B). After 48 hours, the reaction supplemented with NADPH showed no change in isobutanol production, but the ATP supplemented reaction increased isobutanol production by 41% over the control. These results suggest that ATP hydrolysis, whether by ATPase contamination or passive ATP hydrolysis, may be the limiting factor for isobutanol production in this stoichiometric pathway even after multiple attempts to purify away any ATPase contamination.

Design of an ATP Rheostat.

The results so far suggest that ATP depletion is a major problem for the long term sustainability of the stoichiometric reaction system. One way to deal with this problem might be to scrupulously purify all enzymes to eliminate any ATPase activity. But it may never be possible to completely eliminate spontaneous hydrolysis or hydrolysis by imperfect kinase reactions. Moreover, requiring completely pristine enzyme preparations is impractical on a large scale. Thus, a method to restore ATP levels as an intrinsic feature of the system was developed. To this end, a molecular rheostat was used.

The molecular rheostat (FIG. 3A) is made up two competing pathway branches that eventually transform glyceraldehyde-3 phosphate (G3P) into 3-phosphoglycerate (3PG). One branch generates ATP, while flow through the ATP generating branch is regulated by Pi levels. The first branch is made up of one enzyme, the non-phosphorylating GapN used in the stoichiometric pathway, which reduces $NADP^+$ to NADPH and converts G3P directly into 3PG without generating ATP. The second pathway is composed of two enzymes, an NADPH specific, phosphorylating glyceraldehyde-3-phosphate dehydrogenase (GapDH) and phosphoglycerate kinase (PGK), that also produces NADPH but first converts G3P into 1,3-bisphosphoglycerate (1,3BPG) followed by 3PG and ATP by the action of PGK. Therefore, the GapDH/PGK branch produces an additional ATP compared to the GapN only branch.

The relative flow through the ATP generating branch of the rheostat is controlled by free Pi, which acts as a proxy for the amount of ATP hydrolyzed to ADP and Pi. The function of the rheostat is easiest to see in the simplest case, where no exogenous Pi is added to the reaction (FIG. 3A). In this case there is initially no free Pi and there can be no flux through the phosphorylating GAPDH. Thus, in the absence of Pi, all the flux passes through GapN branch. Only when ATP is hydrolyzed to ADP and Pi, can the phosphorylating branch be utilized. Thus, the rheostat senses the depletion of ATP and acts to restore ATP by utilizing the phosphorylating GAPDH branch.

To explore the effectiveness of this design, a computer model of the overall pathway was made with and without the molecular rheostat system using COPASI (FIG. 4). As expected, the stoichiometric pathway, relying on GapN only, gradually winds down when any amount of ATP hydrolysis is introduced, much like what was observed experimentally. When this pathway is augmented with GapDH and PGK to complete the molecular rheostat, the reaction reaches a steady state and proceeds to completion. In this model the molecular rheostat reaches a steady state any time the flux through GapDH and PGK is greater than the ATPase activity that is modeled. This autoregulatory function means that the node will operate at a wide range of ATPase activities and that there is no need to perfectly tune and match the system to the specific amount of ATP hydrolysis for the system to reach a steady state. This autoregulatory behavior for ATP production is a key feature for designing easy to use, self-sustaining in vitro enzymatic pathways. In addition, modeling this pathway computationally allowed quick tests of the rheostat concept under an array of conditions and determine that increasing $P_i$, ATP, and hexokinase should result in an increase in the overall reaction rate.

Engineering Gap M6.

To implement the "molecular rheostat" module, GapDH enzyme was engineered that efficiently uses $NADP^+$. Both the E. coli GapDH (EcGap) and G. stearothermophilus GapDH (GsGap) prefer NAD' over $NADP^+$ although the GsGap displays a higher basal activity with $NADP^+$ than EcGap (which is absolutely specific for $NAD^+$). Although the cofactor specificity of GsGap has adjusted before by sequence-based design, the mutant only slightly preferred $NADP^+$ over $NAD^+$. To more strongly flip the cofactor specificity of GsGap the crystal structure was examined and basic residues introduced into the loop region proximate to the 2'OH of NAD' that may help stabilize binding of a 2' phosphate in $NADP^+$. A series of mutations were made altering residues D34, L35, and T36 of SEQ ID NO:6. The kinetics and specificity of the best enzyme, a D34A/L35R/T36K triple mutant (herein referred to as mGap), were obtained. The wild type GsGap enzyme has only modest activity with $NADP^+$, but the triple mutant mGAP showed much improved activity with NADP at the expense of NAD'.

| Emyme | Cofactor | kcat (μM/min/mg) | KM (mM) | $k_{cat}/K_m$ |
|---|---|---|---|---|
| gapDH WT | NAD+ | 21.8 ± 2.6 | 1.5 ± 0.3 | 14.5 |
| | NADP+ | 1.2 ± 0.1 | 1.5 ± 0.5 | 2.1 |
| mGapDH | NAD+ | 0.2 ± 0.04 | 0.6 ± 0.4 | 0.4 |
| | NADP+ | 3.2 ± 0.1 | 0.3 ± 0.04 | 11.9 |

Isobutanol Production with Molecular Rheostat.

Figure 5A:
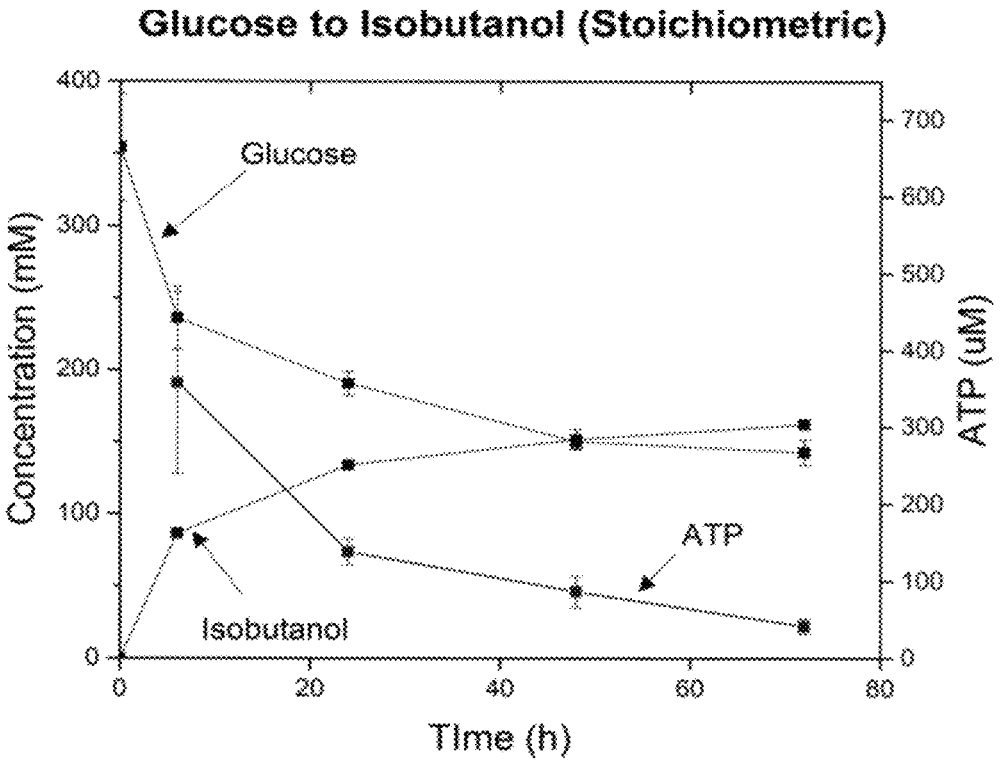
FIG. 5A-C shows the final production of isobutanol. (A) Shows a time course of the isobutanol production, glucose consumption, and ATP in the system using a stoichiometric pathway. (B) Shows a time course of the isobutanol production, glucose consumption and ATP in the ATP rheostat reaction. This reaction created a stead state of ATP at 600 uM and produced 2× as much isobutanol as the stoichiometric pathway. (C) Is a 24 hour histogram of isobutanol production from the stoichiometric system (gapN only), too much ATP production system (gapDH M6 only), and the rheostat system (both gapN and GapDH M6).
Figure 5B:
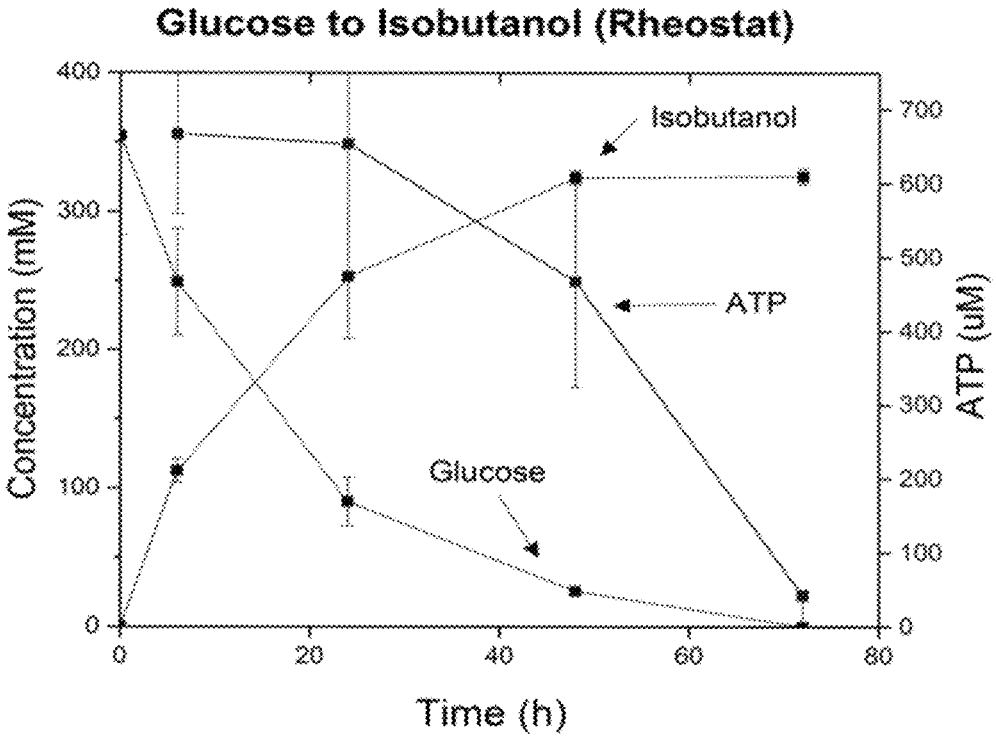

To implement the molecular rheostat for the production of isobutanol from glucose, the two enzymes mGap and PGK were added to the optimized stoichiometric reaction. To ensure sufficient ATP production through the molecular rheostat, the units of mGap and PGK activity in the reaction were an order of magnitude greater than the aggregate ATPase activity in the reaction. Reactions with and without the molecular rheostat were set up side-by-side over a 72 hour time course and were tested for Isobutanol production, residual glucose and ATP (FIG. 5A-B). The reaction with the molecular rheostat produced 24.1±1.8 g/L of isobutanol at 91.5% of the theoretical yield with a maximum productivity of 1.4±0.3 g/L/h. This isobutanol production represents a 101.7% improvement over the stoichiometric in vitro reaction and is higher than any published in vivo isobutanol production without the aid of complex in situ isobutanol removal.

The enzymes and enzyme concentrations in the final preparation pathway (see, e.g., FIG. 6A-B) are presented in the following table:

| Enzyme | Stock concentration (mg/mL) | Enzyme Activity (uM/min/mg) | Units/mL added to reaction |
|---|---|---|---|
| Sc Hk | 2.73 | 7.2 ± 0.1 | 0.025 |
| Gt PgiA | 5.7 | 19.2 ± 0.2 | 1.04 |
| Gs PfkA | 8.49 | 9.6 ± 0.2 | 3.260 |
| Sa FBA | 9.84 | 21.1 ± 0.3 | 8.305 |
| Gs TPI | 12.75 | 96.6 ± 5.4 | 12.317 |
| Sm GapN | 16.09 | 20.6 ± 2.7 | 9.944 |
| Gs Gsp M6 | 4.47 | 7.9 ± 0.4 | 0.177 |
| Gs PGK | 6.28 | 102.3 ± 2.9 | 3.212 |
| Gs PGM | 12.16 | 97.2 ± 13.0 | 17.729 |
| Ec Enolase | 26.09 | 82.5 ± 0.1 | 53.435 |
| Ec Pykf | 16.39 | 365.3 ± 37.9 | 299.363 |
| Bs AlsS | 6.22 | 6.94 ± 1.22 | 1.727 |
| Ec IlvC | 21.43 | 0.88 ± 0.23 | 1.509 |
| Re IlvD | 11.58 | 3.4 ± 0.3[1] | 1.575 |
| Ll KivD | 6.27 | 13.39 ± 2.28 | 0.672 |
| Ec Yahk | 2.18 | 3.64 ± 0.37 | 0.635 |

Figure 5C:
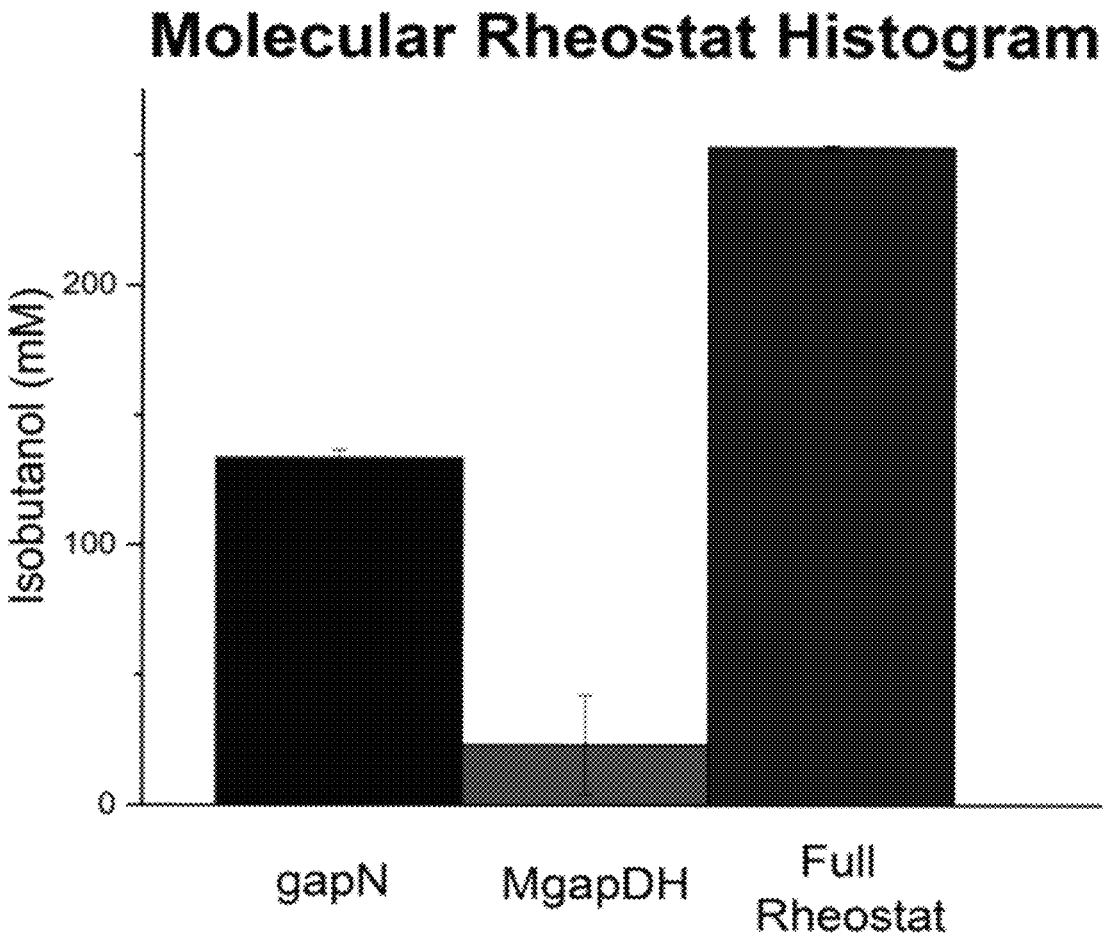

The molecular rheostat performed as expected and maintain a higher ATP concentration relative to the stoichiometricly balanced reaction. The rheostat reaction held a steady state concentration of ATP of around 600 μM over 48 hours before the reaction stopped and the ATP concentration dropped. In contrast, the ATP concentration in the stoichiometric reaction steadily dropped throughout the entire run. Over the first 48 hours of both reactions there is a good correlation between the concentration of ATP in the reaction and the isobutanol productivity. Additionally, each component of the rheostat system was tested by leaving them out of the reaction and measuring the isobutanol produced after 24 hours (FIG. 5C). When either the GapN or mGap/PGK was left out, production of isobutanol was drastically reduced compared to the full molecular rheostat system.

Although the system containing the molecular rheostat produced a self-sustaining reaction and maintained a steady state of ATP for the first 48 hours, the reaction stopped at the 72 hour time point. In the reaction with the molecular rheostat, a precipitate was noticed that began to form after 24 hours which coincided with a decrease in isobutanol production. Upon completion of the reaction the precipitate was collected by centrifugation and separated by SDS-PAGE to identify proteins in the precipitate. Hexokinase was identified as the major constituent of the precipitate followed by KivD, and mGap. These results suggested that some of the enzymes were denaturing over time, possibly due to increasing isobutanol concentrations.

To determine the stability of each system component to isobutanol, each enzyme and cofactor in the pathway was tested for stability in 0%, 4% and 8% (saturating) isobtuanol. Hexokinase, GapN, mGap, and IlvC were most susceptible to isobutanol inactivation while most other enzymes and cofactors maintained significant activity at saturating levels of Isobutanol over 30 hours. These results rapidly identify a handful of priority enzymes that could be targeted for stability improvements to improve the overall sustainability of the system.

A number of embodiments of the invention have been described. Nevertheless, it will be understood that various modifications may be made without departing from the spirit and scope of the invention. Accordingly, other embodiments are within the scope of the following claims.

SEQUENCE LISTING

```
Sequence total quantity: 15
SEQ ID NO: 1            moltype = AA  length = 319
FEATURE                 Location/Qualifiers
source                  1..319
                        mol_type = protein
                        organism = Geobacillus stearothermophilus
SEQUENCE: 1
MKRIGVLTSG GDSPGMNAAI RSVVRKAIYH GVEVYGVYHG YAGLIAGNIK KLEVGDVGDI  60
IHRGGTILYT ARCPEFKTEE GQKKGIEQLK KHGIEGLVVI GGDGSYQGAK KLTEHGFPCV  120
GVPGTIDNDI PGTDFTIGFD TALNTVIDAI DKIRDTATSH ERTYVIEVMG RHAGDIALWS  180
GLAGGAETIL IPEADYDMND VIARLKRGHE RGKKHSIIIV AEGVGSGVDF GRQIQEATGF  240
ETRVTVLGHV QRGGSPTAFD RVLASRLGAR AVELLLEGKG GRCVGIQNNQ LVDHDIAEAL  300
ANKHTIDQRM YALSKELSI                                               319

SEQ ID NO: 2            moltype = AA  length = 253
FEATURE                 Location/Qualifiers
source                  1..253
                        mol_type = protein
                        organism = Geobacillus stearothermophilus
SEQUENCE: 2
MRKPIIAGNW KMHKTLAEAV QFVEDVKGHV PPADEVDSVV CAPFLFLDRL VQAADGTDLK  60
IGAQTMHFAD QGAYTGEVSP VMLKDLGVTY VILGHSERRQ MFAETDETVN KKVLAAFTRG  120
LIPIICCGES LEEREAGQTN AVVASQVEKA LAGLTPEQVK QAVIAYEPIW AIGTGKSSTP  180
EDANSVCGHI RSVVSRLFGP EAAEAIRIQY GGSVKPDNIR DFLAQQQIDG ALVGGASLEP  240
ASFLQLVEAG RHE                                                     253

SEQ ID NO: 3            moltype = AA  length = 299
FEATURE                 Location/Qualifiers
source                  1..299
                        mol_type = protein
                        organism = Staphylococcus aureus
SEQUENCE: 3
MESMNKEQLE KMKNGKGFIA ALDQSGGSTP KALKEYGVNE DQYSNEDEMF QLVHDMRTRV  60
VTSPSFSPDK ILGAILFEQT MDREVESKYT ADYLADKGVV PFLKVDKGLA EEQNGVQLMK  120
PIDNLDNLLD RANERHIFGT KMRSNILELN EQGIKDVVEQ QFEVAKQIIA KGLVPIIEPE  180
VNINAKDKAE IEKVLKAELK KGLDSLNADQ LVMLKLTIPT EPNLYKELAE HPNVVRVVVL  240
SGGYSREKAN ELLKDNAELI ASFSRALASD LRADQSKEEF DKALGDAVES IYDASVNKN   299

SEQ ID NO: 4            moltype = AA  length = 449
FEATURE                 Location/Qualifiers
source                  1..449
                        mol_type = protein
                        organism = Geobacillus thermodenitrificans
SEQUENCE: 4
MTHIRFDYSK ALAFFGEHEL TYLRDAVKVA HHSLHEKTGV GNDFLGWLDW PVNYDKEEFA  60
RIKQAAKKIQ SDSDVLLVIG IGGSYLGARA AIEMLHHSFY NALPKEKRST PQIIFVGNNI  120
SSTYMKDVID FLEGKDFSIN VISKSGTTTE PAIAFRIFRK LLEDKYGKEE ARRRIYATTD  180
RARGALRTLA DEEGYETFVI PDDIGGRYSV LTAVGLLPIA ASGADIDAMM EGAAKAREDF  240
SRSELEENAA YQYAAIRNIL YNKGKTIELL VNYEPALHYF AEWWKQLFGE SEGKDQKGIY  300
PASADFSTDL HSLGQYIQEG RRDLFETVLK LEEPRHELVI EAEESDLDGL NYLAGQTVDF  360
VNTKAFEGTL LAHTDGGVPN LVVTLPKLDE YTFGYLVYFF EKACAMSGYL LGVNPFDQPG  420
VEAYKKNMFA LLGKPGYEEL KDELEKRLK                                    449

SEQ ID NO: 5            moltype = AA  length = 475
FEATURE                 Location/Qualifiers
source                  1..475
                        mol_type = protein
                        organism = Streptococcus mutans
SEQUENCE: 5
MTKQYKNYVN GEWKLSENEI KIYEPASGAE LGSVPAMSTE EVDYVYASAK KAQPAWRSLS  60
YIERAAYLHK VADILMRDKE KIGAVLSKEV AKGYKSAVSE VVRTAEIINY AAEEGLRMEG  120
EVLEGGSFEA ASKKKIAVVR REPVGLVLAI SPFNYPVNLA GSKIAPALIA GNVIAFKPPT  180
QGSISGLLLA EAFAEAGLPA GVFNTITGRG SEIGDYIVEH QAVNFINFTG STGIGERIGK  240
MAGMRPIMLE LGGKDSAIVL EDADLELTAK NIIAGAFGYS GQRCTAVKRV LVMESVADEL  300
VEKIREKVLA LTIGNPEDDA DITPLIDTKS ADYVEGLIND ANDKGAAALT EIKREGNLIC  360
PILFDKVTTD MRLAWEEPFG PVLPIIRVTS VEEAIEISNK SEYGLQASIF TNDFPRAFGI  420
AEQLEVGTVH INNKTQRGTD NFPFLGAKKS GAGIQGVKYS IEAMTTVKSV VFDIK       475

SEQ ID NO: 6            moltype = AA  length = 335
FEATURE                 Location/Qualifiers
source                  1..335
                        mol_type = protein
                        organism = Geobacillus stearothermophilus
SEQUENCE: 6
MAVKVGINGF GRIGRNVFRA ALKNPDIEVV AVNDLTDANT LAHLLKYDSV HGRLDAEVSV  60
NGNNLVVNGK EIIVKAERDP ENLAWGEIGV DIVVESTGRF TKREDAAKHL EAGAKKVIIS  120
APAKNEDITI VMGVNQDKYD PKAHHVISNA SCTTNCLAPF AKVLHEQFGI VRGMMTTVHS  180
YTNDQRILDL PHKDLRRARA AAESIIPTTT GAAKAVALVL PELKGKLNGM AMRVPTPNVS  240
```

```
VVDLVAELEK EVTVEEVNAA LKAAAEGELK GILAYSEEPL VSRDYNGSTV SSTIDALSTM  300
VIDGKMVKVV SWYDNETGYS HRVVDLAAYI ASKGL                             335

SEQ ID NO: 7           moltype = AA  length = 394
FEATURE                Location/Qualifiers
source                 1..394
                       mol_type = protein
                       organism = Geobacillus stearothermophilus
SEQUENCE: 7
MNKKTIRDVD VRGKRVFCRV DFNVPMEQGA ITDDTRIRAA LPTIRYLIEH GAKVILASHL  60
GRPKGKVVEE LRLDAVAKRL GELLERPVAK TNEAVGDEVK AAVDRLNEGD VLLLENVRFY  120
PGEEKNDPEL AKAFAELADL YVNDAFGAAH RAHASTEGIA HYLPAVAGFL MEKELEVLGK  180
ALSNPDRPFT AIIGGAKVKD KIGVIDNLLE KVDNLIIGGG LAYTFVKALG HDVGKSLLEE  240
DKIELAKSFM EKAKEKGVRF YMPVDVVVAD RFANDANTKV VPIDAIPADW SALDIGPKTR  300
ELYRDVIRES KLVVWNGPMG VFEMDAFAHG TKAIAEALAE ALDTYSVIGG GDSAAAVEKF  360
GLADKMDHIS TGGGASLEFM EGKQLPGVVA LEDK                              394

SEQ ID NO: 8           moltype = AA  length = 511
FEATURE                Location/Qualifiers
source                 1..511
                       mol_type = protein
                       organism = Geobacillus stearothermophilus
SEQUENCE: 8
MSKKPVALII LDGFALRDET YGNAVAQANK PNFDRYWNEY PHTTLKACGE AVGLPEGQMG  60
NSEVGHLNIG AGRIVYQSLT RINIAIREGE FDRNETFLAA MNHVKQHGTS LHLFGLLSDG  120
GVHSHIHHLY ALLRLAAKEG VKRVYIHGFL DGRDVGPQTA PQYIKELQEK IKEYGVGEIA  180
TLSGRYYSMD RDKRWDRVEK AYRAMVYGEG PTYRDPLECI EDSYKHGIYD EFVLPSVIVR  240
EDGRPVATIQ DNDAIIFYNF RPDRAIQISN TFTNEDFREF DRGPKHPKHL FFVCLTHFSE  300
TVKGYVAFKP TNLDNTIGEV LSQHGLRQLR IAETEKYPHV TFFMSGGREE KFPGEDRILI  360
NSPKVPTYDL KPEMSAYEVT DALLKEIEAD KYDAIILNYA NPDMVGHSGK LEPTIKAVEA  420
VDECLGKVVD AILAKGGIAI ITADHGNADE VLTPDGKPQT AHTTNPVPVI VTKKGIKLRD  480
GGILGDLAPT MLDLLGLPQP KEMTGKSLIV K                                 511

SEQ ID NO: 9           moltype = AA  length = 432
FEATURE                Location/Qualifiers
source                 1..432
                       mol_type = protein
                       organism = Escherichia coli
SEQUENCE: 9
MSKIVKIIGR EIIDSRGNPT VEAEVHLEGG FVGMAAAPSG ASTGSREALE LRDGDKSRFL  60
GKGVTKAVAA VNGPIAQALI GKDAKDQAGI DKIMIDLDGT ENKSKFGANA ILAVSLANAK  120
AAAAAKGMPL YEHIAELNGT PGKYSMPVPM MNIINGGEHA DNNVDIQEFM IQPVGAKTVK  180
EAIRMGSEVF HHLAKVLKAK GMNTAVGDEG GYAPNLGSNA EALAVIAEAV KAAGYELGKD  240
ITLAMDCAAS EFYKDGKYVL AGEGNKAFTS EEFTHFLEEL TKQYPIVSIE DGLDESDWDG  300
FAYQTKVLGD KIQLVGDDLF VTNTKILKEG IEKGIANSIL IKFNQIGSLT ETLAAIKMAK  360
DAGYTAVISH RSGETEDATI ADLAVGTAAG QIKTGSMSRS DRVAKYNQLI RIEEALGEKA  420
PYNGRKEIKG QA                                                      432

SEQ ID NO: 10          moltype = AA  length = 470
FEATURE                Location/Qualifiers
source                 1..470
                       mol_type = protein
                       organism = Escherichia coli
SEQUENCE: 10
MKKTKIVCTI GPKTESEEML AKMLDAGMNV MRLNFSHGDY AEHGQRIQNL RNVMSKTGKT  60
AAILLDTKGP EIRTMKLEGG NDVSLKAGQT FTFTTDKSVI GNSEMVAVTY EGFTTDLSVG  120
NTVLVDDGLI GMEVTAIEGN KVICKVLNNG DLGENKGVNL PGVSIALPAL AEKDKQDLIF  180
GCEQGVDFVA ASFIRKRSDV IEIREHLKAH GGENIHIISK IENQEGLNNF DEILEASDGI  240
MVARGDLGVE IPVEEVIFAQ KMMIEKCIRA RKVVITATQM LDSMIKNPRP TRAEAGDVAN  300
AILDGTDAVM LSGESAKGKY PLEAVSIMAT ICERTDRVMN SRLEFNNDNR KLRITEAVCR  360
GAVETAEKLD APLIVVATQG GKSARAVRKY FPDATILALT TNEKTAHQLV LSKGVVPQLV  420
KEITSTDDFY RLGKELALQS GLAHKGDVVV MVSGALVPSG TTNTASVHVL             470

SEQ ID NO: 11          moltype = AA  length = 571
FEATURE                Location/Qualifiers
source                 1..571
                       mol_type = protein
                       organism = Bacillus subtilis
SEQUENCE: 11
MLTKATKEQK SLVKNRGAEL VVDCLVEQGV THVFGIPGAK IDAVFDALQD KGPEIIVARH  60
EQNAAFMAQA VGRLTGKPGV VLVTSGPGAS NLATGLLTAN TEGDPVVALA GNVIRADRLK  120
RTHQSLDNAA LFQPITKYSV EVQDVKNIPE AVTNAFRIAS AGQAGAAFVS FPQDVVNEVT  180
NTKNVRAVAA PKLGPAADDA ISAAIAKIQT AKLPVVLVGM KGGRPEAIKA VRKLLKKVQL  240
PFVETYQAAG TLSRDLEDQY FGRIGLFRNQ PGDLLLEQAD VVLTIGYDPI EYDPKFWNIN  300
GDRTIIHLDE IIADIDHAYQ PDLELIGDIP STINHIEHDA VKVEFAEREQ KILSDLKQYM  360
HEGEQVPADW KSDRAHPLEI VKELRNAVDD HVTVTCDIGS HAIWMSRYFR SYEPLTLMIS  420
NGMQTLGVAL PWAIGASLVK PGEKVVSVSG DGGFLFSAME LETAVRLKAP IVHIVWNDST  480
YDMVAFQQLK KYNRTSAVDF GNIDIVKYAE SFGATGLRVE SPDQLADVLR QGMNAEGPVI  540
IDVPVDYSDN INLASDKLPK EFGELMKTKA L                                 571
```

```
SEQ ID NO: 12          moltype = AA  length = 491
FEATURE                Location/Qualifiers
source                 1..491
                       mol_type = protein
                       organism = Escherichia coli
SEQUENCE: 12
MANYFNTLNL RQQLAQLGKC RFMGRDEFAD GASYLQGKKV VIVGCGAQGL NQGLNMRDSG  60
LDISYALRKE AIAEKRASWR KATENGFKVG TYEELIPQAD LVINLTPDKQ HSDVVRTVQP  120
LMKDGAALGY SHGFNIVEVG EQIRKDITVV MVAPKCPGTE VREEYKRGFG VPTLIAVHPE  180
NDPKGEGMAI AKAWAAATGG HRAGVLESSF VAEVKSDLMG EQTILCGMLQ AGSLLCFDKL  240
VEEGTDPAYA EKLIQFGWET ITEALKQGGI TLMMDRLSNP AKLRAYALSE QLKEIMAPLF  300
QKHMDDIISG EFSSGMMADW ANDDKKLLTW REETGKTAFE TAPQYEGKIG EQEYFDKGVL  360
MIAMVKAGVE LAFETMVDSG IIEESAYYES LHELPLIANT IARKRLYEMN VVISDTAEYG  420
NYLFSYACVP LLKPFMAELQ PGDLGKAIPE GAVDNGQLRD VNEAIRSHAI EQVGKKLRGY  480
MTDMKRIAVA G                                                       491

SEQ ID NO: 13          moltype = AA  length = 616
FEATURE                Location/Qualifiers
source                 1..616
                       mol_type = protein
                       organism = Escherichia coli
SEQUENCE: 13
MPKYRSATTT HGRNMAGARA LWRATGMTDA DFGKPIIAVV NSFTQFVPGH VHLRDLGKLV  60
AEQIEAAGGV AKEFNTIAVD DGIAMGHGGM LYSLPSRELI ADSVEYMVNA HCADAMVCIS  120
NCDKITPGML MASLRLNIPV IFVSGGPMEA GKTKLSDQII KLDLVDAMIQ GADPKVSDSQ  180
SDQVERSACP TCGSCSGMFT ANSMNCLTEA LGLSQPGNGS LLATHADRKQ LFLNAGKRIV  240
ELTKRYYEQN DESALPRNIA SKAAFENAMT LDIAMGGSTN TVLHLLAAAQ EAEIDFTMSD  300
IDKLSRKVPQ LCKVAPSTQK YHMEDVHRAG GVIGILGELD RAGLLNRDVK NVLGLTLPQT  360
LEQYDVMLTQ DDAVKNMFRA GPAGIRTTQA FSQDCRWDTL DDDRANGCIR SLEHAYSKDG  420
GLAVLYGNFA ENGCIVKTAG VDDSILKFTG PAKVYESQDD AVEAILGGKV VAGDVVVIRY  480
EGPKGGPGMQ EMLYPTSFLK SMGLGKACAL ITDGRFSGGT SGLSIGHVSP EAASGGSIGL  540
IEDGDLIAID IPNRGIQLQV SDAELAARRE AQDARGDKAW TPKNRERQVS FALRAYASLA  600
TSADKGAVRD KSKLGG                                                  616

SEQ ID NO: 14          moltype = AA  length = 548
FEATURE                Location/Qualifiers
source                 1..548
                       mol_type = protein
                       organism = Lactococcus lactis
SEQUENCE: 14
MYTVGDYLLD RLHELGIEEI FGVPGDYNLQ FLDQIISRKD MKWVGNANEL NASYMADGYA  60
RTKKAAAFLT TFGVGELSAV NGLAGSYAEN LPVVEIVGSP TSKVQNEGKF VHHTLADGDF  120
KHFMKMHEPV TAARTLLTAE NATVEIDRVL SALLKERKPV YINLPVDVAA AKAEKPSLPL  180
KKENSTSNTS DQEILNKIQE SLKNAKKPIV ITGHEIISFG LEKTVSQFIS KTKLPITTLN  240
FGKSSVDEAL PSFLGIYNGK LSEPNLKEFV ESADFILMLG VKLTDSSTGA FTHHLNENKM  300
ISLNIDEGKI FNESIQNFDF ESLISSLLDL SEIEYKGKYI DKKQEDFVPS NALLSQDRLW  360
QAVENLTQSN ETIVAEQGTS FFGASSIFLK PKSHFIGQPL WGSIGYTFPA ALGSQIADKE  420
SRHLLFIGDG SLQLTVQELG LAIREKINPI CFIINNDGYT VEREIHGPNQ SYNDIPMWNY  480
SKLPESFGAT EERVVSKIVR TENEFVSVMK EAQADPNRMY WIELILAKED APKVLKKMGK  540
LFAEQNKS                                                           548

SEQ ID NO: 15          moltype = AA  length = 349
FEATURE                Location/Qualifiers
source                 1..349
                       mol_type = protein
                       organism = Escherichia coli
SEQUENCE: 15
MKIKAVGAYS AKQPLEPMDI TRREPGPNDV KIEIAYCGVC HSDLHQVRSE WAGTVYPCVP  60
GHEIVGRVVA VGDQVEKYAP GDLVGVGCIV DSCKHCEECE DGLENYCDHM TGTYNSPTPD  120
EPGHTLGGYS QQIVVHERYV LRIRHPQEQL AAVAPLLCAG ITTYSPLRHW QAGPGKKVGV  180
VGIGGLGHMG IKLAHAMGAH VVAFTTSEAK REAAKALGAD EVVNSRNADE MAAHLKSFDF  240
ILNTVAAPHN LDDFTTLLKR DGTMTLVGAP ATPHKSPEVF NLIMKRRAIA GSMIGGIPET  300
QEMLDFCAEH GIVADIEMIR ADQINEAYER MLRGDVKYRF VIDNRTLTD              349
```

What is claimed is:

[1. A recombinant, artificial or engineered metabolic pathway comprising a plurality of enzymatic steps that converts a substrate to a product, wherein the metabolic pathway comprises:

a non-naturally occurring molecular rheostat system in which two distinct cofactor-dependent enzymatic pathways convert a first metabolite in the metabolic pathway to a downstream second metabolite within the metabolic pathway and wherein the distinct cofactor dependent enzymatic pathways produce different intermediate metabolites using a first distinct cofactor, wherein the first distinct enzymatic pathway provides an enzyme that directly converts the first metabolite to the downstream second metabolite, and wherein the second distinct enzymatic pathway provides a plurality of enzymes that converts the first metabolite to the downstream second metabolite, wherein the molecular rheostat alternates between or simultaneously uses the two distinct cofactor-dependent enzymatic pathways for the production of the downstream second metabolite depending upon the availability of a second distinct cofactor.]

[2. A recombinant, artificial or engineered metabolic pathway of claim 1, wherein the first distinct enzymatic pathway is active when the co-factor utilized by the second distinct enzymatic pathway level is low and wherein the second distinct enzymatic pathway is active when this co-factor level is high.]

[3. The recombinant, artificial or engineered pathway of claim 1, wherein the first cofactor utilized by the first distinct enzymatic pathway is an oxidizing/reducing co-factors and the second distinct enzymatic pathway cofactor is Pi.]

[4. The recombinant, artificial or engineered pathway of claim 3, wherein the oxidizing/reducing co-factors are $NAD^+$/NADH, $NADP^+$/NADPH or $FAD^+$/FADH.]

[5. The recombinant, artificial or engineered pathway of claim 4, wherein the cofactor comprises $NADP^+$/NADPH.]

[6. The recombinant, artificial or engineered metabolic pathway of claim 1, wherein the metabolic pathway comprises the conversion of glyceraldehyde-3-phosphate to 3-phosphoglycerate.]

[7. The recombinant, artificial or engineered metabolic pathway of claim 6, wherein the metabolic pathway produces a product selected from the group consisting of isobutanol, 3-methyl-1-butanol, leucine, and valine.]

[8. The recombinant, artificial or engineered metabolic pathway of claim 6, wherein the second distinct enzymatic pathway comprises the conversion of glyceraldehyde-3-phosphate to 1,3-bisphosphoglycerate and 1,3-bisphosphoglycerate to 3-phosphoglycerate.]

[9. The recombinant artificial or engineered metabolic pathway of claim 6, wherein:

(i) the first distinct enzyme pathway converts glyceraldehyde-3-phosphate (G3P) and $NADP^+$ to 3-phosphoglycerate (3PG) and NADPH; and (ii) the second enzyme pathway converts glyceraldehyde-3-phosphate (G3P), NADP+, and free phosphate (Pi) to 1,3-bisphosphoglycerate (1,3BPG) and converts 1,3 bisphosphoglycerate (1,3BPG) and ADP to 3-phosphoglycerate and ATP.]

[10. The recombinant artificial or engineered metabolic pathway of claim 9, wherein the enzyme of (i) comprises a NADP-dependent glyceraldehyde-3-phosphate dehydrogenase (GapN).]

[11. The recombinant artificial or engineered metabolic pathway of claim 10, wherein the GapN is obtained from Streptococcus mutans.]

[12. The recombinant artificial or engineered metabolic pathway of claim 9, wherein the enzyme of (ii) comprises a mutant glyceraldehyde-3-phosphate dehydrogenase (mGap) that comprises D34A/L35R/T36K mutations relative to SEQ ID NO: 6.]

[13. The recombinant artificial or engineered metabolic pathway of claim 9, wherein the enzyme of (ii) comprises a mutant glyceraldehyde-3-phosphate dehydrogenase (mGap) that has a sequence that shares is at least 95% sequence identity to SEQ ID NO: 6 and comprises D34A/L35R/T36K mutations.]

[14. The recombinant artificial or engineered metabolic pathway of claim 9, wherein an enzyme that converts 1,3 bisphosphoglycerate (1,3BPG) and ADP to 3-phosphoglycerate and ATP comprises an enzyme from enzyme commission number (EC number) EC 2.7.2.3.]

[15. The recombinant artificial or engineered metabolic pathway of claim 14, wherein the enzyme is a phosphoglycerate kinase.]

[16. The recombinant artificial or engineered metabolic pathway of claim 15, wherein the phosphoglycerate kinase is a Pgk from Geobacillus stearothermophilus.]

[17. The recombinant artificial or engineered metabolic pathway of claim 15, wherein the enzyme has a sequence that shares is at least 95% sequence identity to SEQ ID NO: 7 and has phosphoglycerate kinase activity.]

[18. The recombinant artificial or engineered metabolic pathway of claim 9, wherein the molecular rheostat comprise the enzymes of (i) a NADP-dependent glyceraldehyde-3-phosphate dehydrogenase (GapN), (ii) a mutant glyceraldehyde-3-phosphate dehydrogenase that utilizes $NADP^+$ and (iii) a phosphoglycerate kinase.]

[19. The recombinant artificial or engineered metabolic pathway of claim 1, wherein the pathway comprises:

(i) an enzyme that catalyzes the production of glucose-6-phosphate (G6P) from glucose;

(ii)) an enzyme that catalyzes the production of Fructose-6-phosphate (FGP) from glucose-6-phosphate (G6P);

(iii)) an enzyme that catalyzes the conversion/phosphorylation of fructose-6-phosphate (F6P) to fructose-1,6-phosphate;

(iv)) an enzyme that converts fructose-1,6-phosphate to two glyceraldehyde-3-phosphates (G3P);

(v) a molecular rheostat comprising:

(a) an enzyme that converts glyceraldehyde-3-phosphate (G3P) and NADP+ to 3-phosphoglycerate (3PG) and NADPH and (b) an enzyme that converts glyceraldehyde-3-phosphate (G3P), NADP+ and free phosphate (Pi) to 1,3-bisphosphoglycerate (1,3BPG) and (c) an enzyme that converts 1,3 bisphosphglycerate (1,3BPG) and ADP to 3-phophoglycerate (3PG) and ATP;

(vi) a polypeptide that converts 3-phosphoglycerate (3PG) to 2-phosphoglycerate (2PG);

(vii)) an enzyme that converts 2-phosphoglycerate (2PG) to phosphoenolpyruvate (PEP);

(vii)) an enzyme that converts phosphoenolpyruvate (PEP) to pyruvate;

(ix)) an enzyme that converts pyruvate to acetolactate; (x) a polypeptide that converts acetolactate and NADPH to 2,3 dihydroxy-3-methyl butanoate and $NADP^+$;

(xi) a polypeptide that converts 2,3 dihydroxy-3-methyl butanoate to 3-methyl-2-oxobutanoate;

(xii)) an enzyme that converts 3-methyl-2-oxobutanoate to isobutanal; and (xiii) a polypeptide that coverts isobutanal and NADPH to isobutanol and $NADP^+$.]

[20. The recombinant, artificial or engineered pathway of claim 1, wherein the metabolic pathway is in a cell-free system.]

[21. A recombinant polypeptide comprising a sequence that shares at least 95% sequence identity to SEQ ID NO: 6 and comprises D34A/L35R/T36K mutations and has glyceraldehyde-3-phosphate dehydrogenase activity.]

*22. A metabolic pathway that converts a substrate to a product, wherein the metabolic pathway comprises:*

*a non-naturally occurring molecular rheostat system in which two distinct cofactor-dependent enzymatic pathways convert the substrate in the metabolic pathway to the product within the metabolic pathway;*

*wherein the first distinct enzymatic pathway provides at least one first enzyme that directly converts the substrate to the product in the presence of an oxidizing/reducing cofactor;*

*wherein the second distinct enzymatic pathway provides at least one second enzyme that converts the substrate to the product in the presence of the oxidizing/reducing cofactor and free phosphate (Pi); and*

*wherein the non-naturally occurring molecular rheostat system alternates between or simultaneously uses the two distinct cofactor-dependent enzymatic pathways for the production of the product depending upon availability of Pi.*

*23. The metabolic pathway of claim 22, wherein the first distinct enzymatic pathway is active when the availability of Pi is low and wherein the second distinct enzymatic pathway is active when the availability of Pi is high.*

*24. The metabolic pathway of claim 22, wherein the oxidizing/reducing cofactor comprises NAD+/NADH, NADP+/NADPH, FAD+/FADH, or ADP/ATP.*

*25. The metabolic pathway of claim 22, wherein the metabolic pathway comprises the conversion of glyceraldehyde-3-phosphate (GBP) to 3-phosphoglycerate (3PG).*

*26. The metabolic pathway of claim 22, wherein the metabolic pathway produces the product selected from the group consisting of isobutanol, 3-methyl-1-butanol, leucine, and valine.*

*27. The metabolic pathway of claim 22, wherein the second distinct enzymatic pathway comprises conversion of glyceraldehyde-3-phosphate (G3P) to 1,3-bisphosphoglycerate (1 ,BBPG) and 1,3-bisphosphoglycerate (1 ,BBPG) to 3-phosphoglycerate (3PG).*

*28. The metabolic pathway of claim 25, wherein:*

*(i) the first distinct enzymatic pathway converts glyceraldehyde-3-phosphate (G3P) and NADP+to 3-phosphoglycerate (3PG) and NADPH; and*

*(ii) the second enzymatic pathway converts glyceraldehyde-3-phosphate (G3P), NADP+, and free phosphate (Pi) to 1,3-bisphosphoglycerate (1,38PG) and converts 1,3 bisphosphoglycerate (1 ,BBPG) and ADP to 3-phosphoglycerate (3PG) and ATP.*

*29. The metabolic pathway of claim 28, wherein first distinct enzymatic pathway utilizes an enzyme comprising a NADP-dependent glyceraldehyde-3-phosphate dehydrogenase (GapN).*

*30. The metabolic pathway of claim 29, wherein the GapN is obtained from Streptococcus mutans.*

*31. The metabolic pathway of claim 28, wherein the second distinct enzymatic pathway utilizes an enzyme comprising a mutant glyceraldehyde-3-phosphate dehydrogenase (mGap), wherein the mGap shares at least 90% sequence identity to SEQ ID NO: 6.*

*32. The metabolic pathway of claim 28, wherein the second distinct enzymatic pathway utilizes an enzyme comprising a mutant glyceraldehyde-3-phosphate dehydrogenase (mGap),*

*wherein the mGap has a sequence that shares at least 90% sequence identity to SEQ ID NO: 6 and comprises a D34A, a L35R and a T36K mutation.*

*33. The metabolic pathway of claim 28, wherein an enzyme from enzyme commission number (EC number) EC 2.7.2.3 converts 1,3 bisphosphoglycerate (1 ,3BPG) and ADP to 3-phosphoglycerate (3PG) and ATP.*

*34. The metabolic pathway of claim 33, wherein the enzyme is a phosphoglycerate kinase.*

*35. The metabolic pathway of claim 34, wherein the phosphoglycerate kinase is a Pqk from Geobaci/lus stearothermophilus.*

*36. The metabolic pathway of claim 34, wherein the enzyme has a sequence that shares at least 90% sequence identity to SEQ ID NO: 7 and has phosphoglycerate kinase activity.*

*37. The metabolic pathway of claim 22, wherein the non-naturally occurring molecular rheostat system comprises enzymes including (i) a NADP-dependent glyceraldehyde-3-phosphate dehydrogenase (GapN), (ii) a mutant glyceraldehyde-3-phosphate dehydrogenase (mGap) that utilizes NADP+, and (iii) a phosphoglycerate kinase.*

*38. The metabolic pathway of claim 22, wherein the metabolic pathway comprises one or more of the following:*

*(i) a first enzyme that catalyzes the production of glucose-6-phosphate (G6P) from glucose;*

*(ii) a second enzyme that catalyzes the production of fructose-6-phosphate (FGP) from glucose-6-phosphate (G6P);*

*(iii) a third enzyme that catalyzes the conversion/phosphorylation of fructose-6-phosphate (F6P) to fructose-1,6-phosphate;*

*(iv) a fourth enzyme that converts fructose-1,6-phosphate to two glyceraldehyde-3-phosphates (G3P);*

*(v) the non-naturally occurring molecular rheostat system comprising:*

*(a) a fifth enzyme that converts glyceraldehyde-3-phosphate (G3P) and NADP+to 3-phosphoglycerate (3PG) and NADPH;*

*(b) a sixth enzyme that converts glyceraldehyde-3-phosphate (G3P), NADP+and free phosphate (Pi) to 1,3-bisphosphoglycerate (1 ,BBPG);*

*(c) a seventh enzyme that converts 1,3 bisphosphglycerate (1 ,BBPG) and ADP to 3-phophoglycerate (3PG) and ATP;*

*(vi) a first polypeptide that converts 3-phosphoglycerate (3PG) to 2-phosphoglycerate (2PG);*

*(vii) an eighth enzyme that converts 2-phosphoglycerate (2PG) to phosphoenolpyruvate (PEP);*

*(viii) a ninth enzyme that converts phosphoenolpyruvate (PEP) to pyruvate;*

*(ix) a tenth enzyme that converts pyruvate to acetolactate;*

*(x) a second polypeptide that converts acetolactate and NADPH to 2,3 dihydroxy-3-methyl butanoate and NADP+;*

*(xi) a third polypeptide that converts 2,3 dihydroxy-3-methyl butanoate to 3-methyl-2-oxobutanoate;*

*(xii) an eleventh enzyme that converts 3-methyl-2-oxobutanoate to isobutanal; and*

*(xiii) a fourth polypeptide that converts isobutanal and NADPH to isobutanol and NADP+.*

*39. The metabolic pathway of claim 22, wherein the metabolic pathway is in a cell-free system.*

*40. A recombinant polypeptide comprising a sequence that shares at least 90% sequence identity to SEQ ID NO: 6, comprises a D34A, a L35R and aT36K mutation, and has glyceraldehyde-3-phosphate dehydrogenase activity.*

* * * * *